(12) United States Patent
Everitt et al.

(10) Patent No.: US 12,629,085 B2
(45) Date of Patent: May 19, 2026

(54) SYSTEM AND METHODS FOR IMPEDANCE-BASED NON-INVASIVE INTRACRANIAL MONITORING

(71) Applicant: TRUSTEES OF DARTMOUTH COLLEGE, Hanover, NH (US)

(72) Inventors: Alicia Everitt, West Lebanon, NH (US); Ryan Halter, Lyme, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 971 days.

(21) Appl. No.: 17/771,273

(22) PCT Filed: Oct. 23, 2020

(86) PCT No.: PCT/US2020/057213
§ 371 (c)(1),
(2) Date: Apr. 22, 2022

(87) PCT Pub. No.: WO2021/081443
PCT Pub. Date: Apr. 29, 2021

(65) Prior Publication Data
US 2022/0361803 A1 Nov. 17, 2022

Related U.S. Application Data

(60) Provisional application No. 62/925,082, filed on Oct. 23, 2019.

(51) Int. Cl.
A61B 5/00 (2006.01)
A61B 5/053 (2021.01)

(52) U.S. Cl.
CPC ............ A61B 5/4064 (2013.01); A61B 5/053 (2013.01)

(58) Field of Classification Search
CPC ..... A61B 5/4064; A61B 5/053; A61B 5/0042; A61B 5/0537; A61B 2562/04
See application file for complete search history.

(56) References Cited

U.S. PATENT DOCUMENTS

2011/0288400 A1 11/2011 Russell et al.
2013/0274615 A1* 10/2013 Ben-Ari ............... A61B 5/0205
600/483

(Continued)

FOREIGN PATENT DOCUMENTS

EP 2 919 647 A1 9/2015
WO WO-2013/153454 A2 10/2013

(Continued)

OTHER PUBLICATIONS

European Communication pursuant to Rules 161(2) and 162 EPC issued Jul. 5, 2022, in corresponding European Patent Application No. 20879007.1, 3 pages.

(Continued)

*Primary Examiner* — May A Abouelela
*Assistant Examiner* — Yasmeen S Warsi
(74) *Attorney, Agent, or Firm* — Oblon, McClelland, Maier & Neustadt, L.L.P.

(57) ABSTRACT

Disclosed is a system for evaluating brain trauma via regional changes in tissue impedance. The present disclosure describes a system for non-invasive intracranial monitoring, comprising two or more affecting electrodes arranged between a conductive location of a cranium of a patient and a location on a scalp of the patient, two or more effected electrodes arranged between the conductive location of the cranium of the patient and the location on the scalp of the patient, and processing circuitry configured to apply an electrical stimulus between the two or more affecting electrodes, measure an electrical stimulus differential between the two or more effected electrodes, calculate, for the two or (Continued)

more effected electrodes, a value of an impedance metric, and identify, based on the calculated value of the impedance metric, a health condition of the patient.

16 Claims, 15 Drawing Sheets

(56) References Cited

U.S. PATENT DOCUMENTS

| | | | |
|---|---|---|---|
| 2014/0358016 A1* | 12/2014 | Shapira | A61B 5/6817 |
| | | | 600/506 |
| 2016/0235352 A1 | 8/2016 | DiLorenzo | |
| 2019/0117976 A1 | 4/2019 | Belson et al. | |

FOREIGN PATENT DOCUMENTS

| | | |
|---|---|---|
| WO | WO-2014/076698 A1 | 5/2014 |
| WO | WO 2021/081443 A1 | 4/2021 |

OTHER PUBLICATIONS

Canadian Office Action issued Nov. 18, 2024 in Canadian Patent Application No. 3,155,931, 7 pages.

Office Action issued Nov. 9, 2023, in corresponding Canadian Patent Application No. 3,155,931, 4 pages.

International Search Report and Written Opinion issued on Jan. 25, 2021 in PCT/US2020/057213 filed Oct. 23, 2020, 11 pages.

Korean Office Action issued Nov. 14, 2025 in Korean Patent Application No. 10-2022-7016909 (with English translation), 13 pages.

Brazilian Office Action issued Nov. 18, 2025 in Brazilian Patent Application No. BR112022007806-4 (with partial English translation), 5 pages.

European Office Action issued Dec. 18, 2025 in European Patent Application No. 20879007.1, 6 pages.

* cited by examiner

210

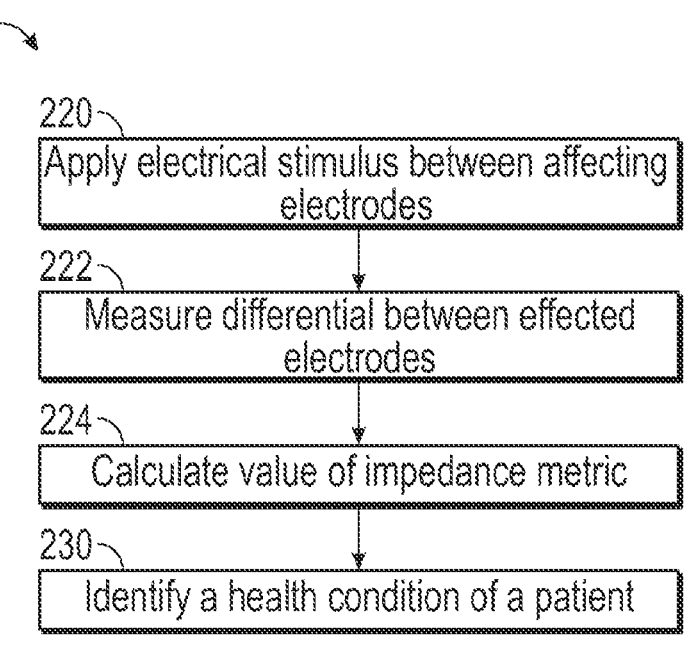

220

Apply electrical stimulus between affecting electrodes

222

Measure differential between effected electrodes

224

Calculate value of impedance metric

230

Identify a health condition of a patient

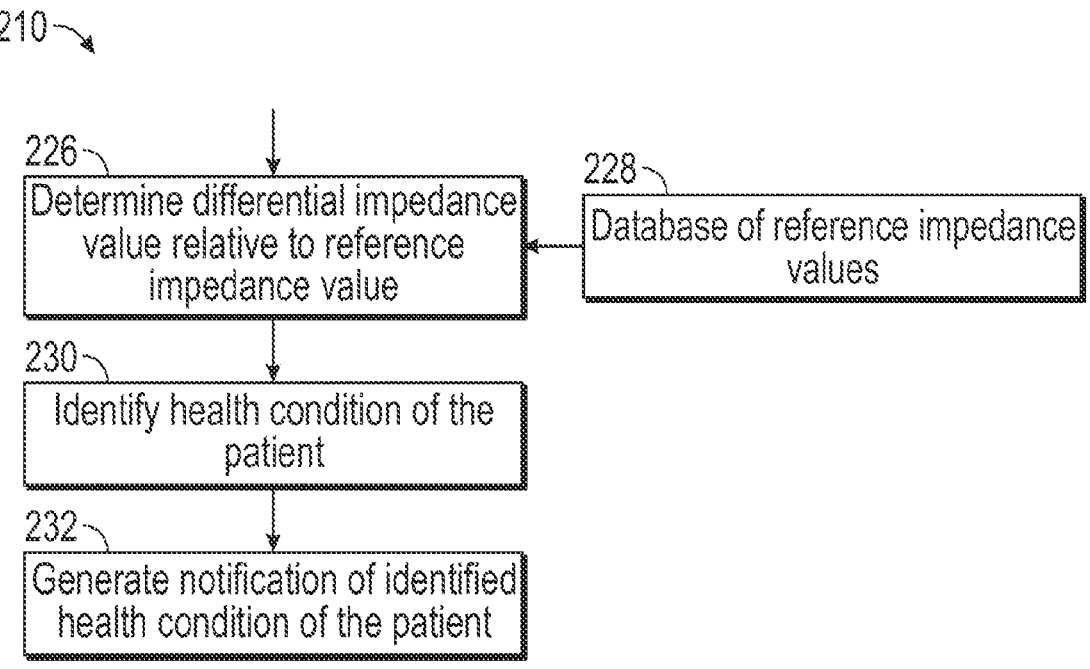

226

Determine differential impedance value relative to reference impedance value

228

Database of reference impedance values

230

Identify health condition of the patient

232

Generate notification of identified health condition of the patient

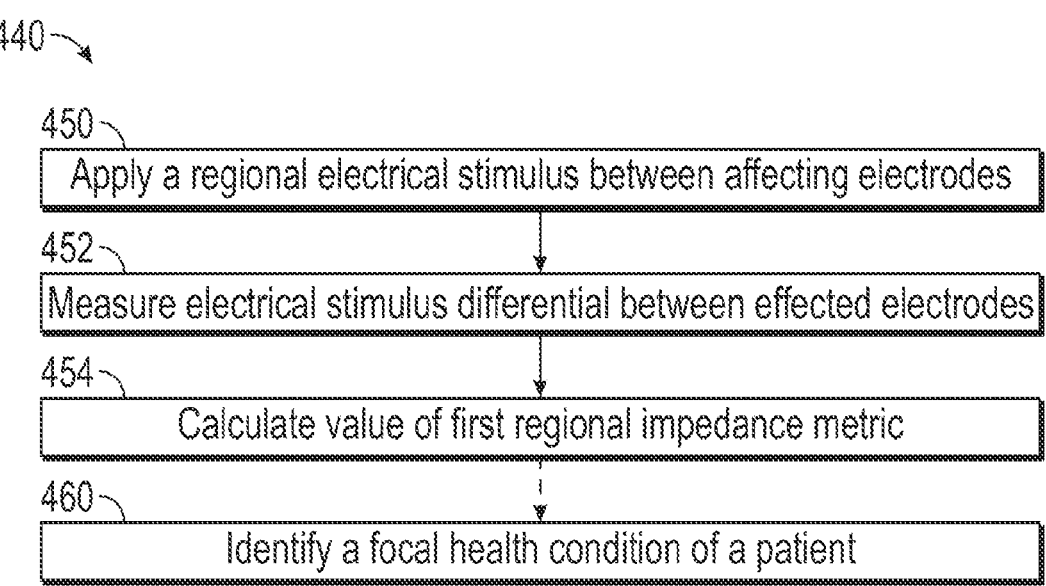

450 Apply a regional electrical stimulus between affecting electrodes

452 Measure electrical stimulus differential between effected electrodes

454 Calculate value of first regional impedance metric

460 Identify a focal health condition of a patient

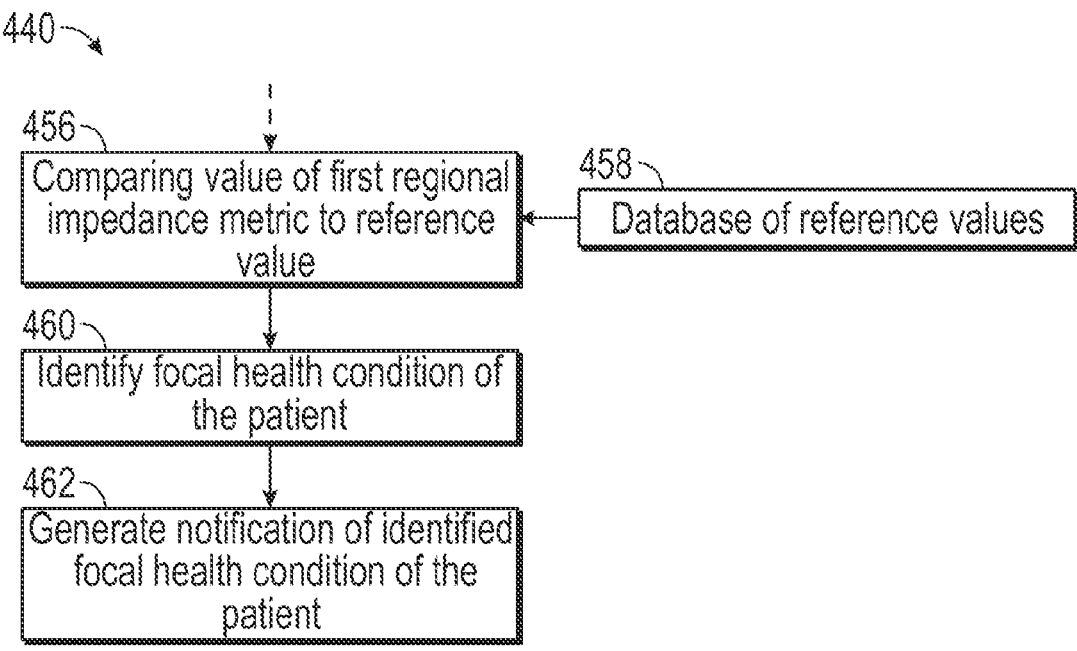

456 Comparing value of first regional impedance metric to reference value

458 Database of reference values

460 Identify focal health condition of the patient

462 Generate notification of identified focal health condition of the patient

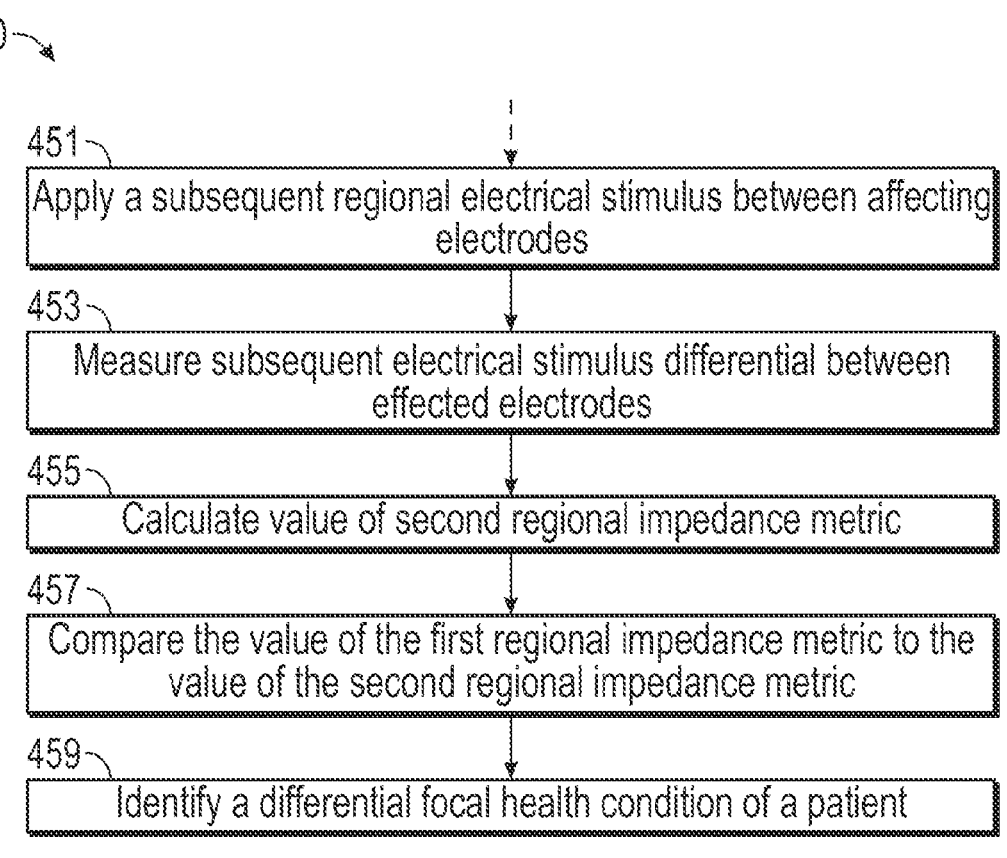

451 — Apply a subsequent regional electrical stimulus between affecting electrodes 453 — Measure subsequent electrical stimulus differential between effected electrodes 455 — Calculate value of second regional impedance metric 457 — Compare the value of the first regional impedance metric to the value of the second regional impedance metric 459 — Identify a differential focal health condition of a patient

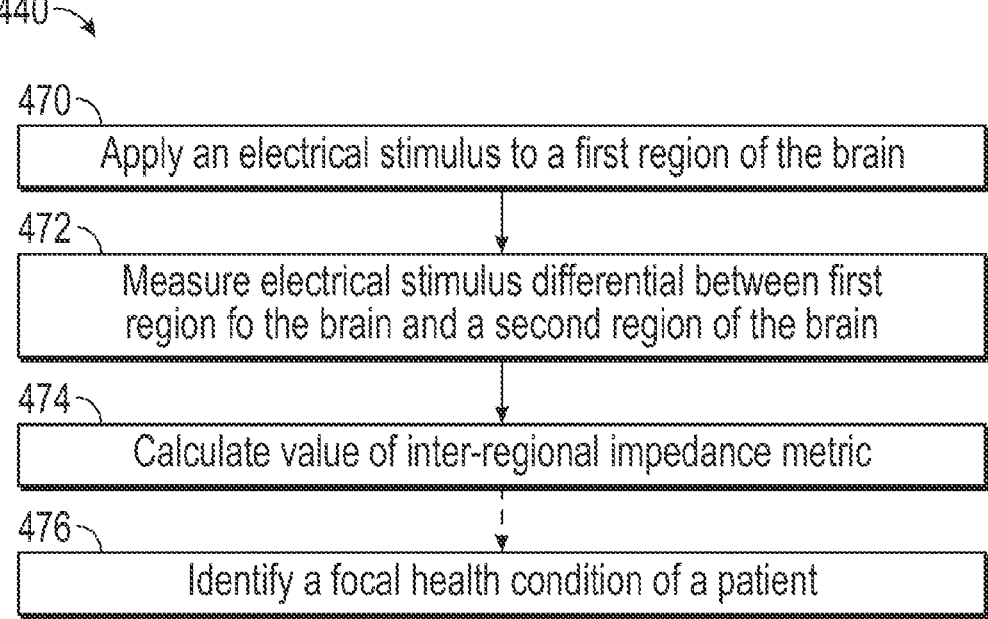

470 — Apply an electrical stimulus to a first region of the brain

472 — Measure electrical stimulus differential between first region fo the brain and a second region of the brain 474 — Calculate value of inter-regional impedance metric 476 — Identify a focal health condition of a patient

SYSTEM AND METHODS FOR IMPEDANCE-BASED NON-INVASIVE INTRACRANIAL MONITORING

CROSS-REFERENCE TO RELATED APPLICATIONS

The present application claims priority to U.S. Provisional Application No. 62/925,082, filed Oct. 23, 2019, the teaching of which is incorporated by reference herein in its entirety for all purposes.

STATEMENT REGARDING GOVERNMENT SUPPORT

This invention was made with government support under 1R41NS100313-01 awarded by National Institutes of Health and under Granite State Technology Innovation Grant awarded by New Hampshire Innovation Research Center. The government has certain rights to the invention.

BACKGROUND

Field of the Disclosure

The present disclosure relates to intracranial monitoring.

Description of the Related Art

The intracranial space is notoriously difficult to monitor without a computed tomography or magnetic resonance imaging scan. Bedside monitoring capabilities are limited to intracranial pressure sensors which only provide a single point metric incapable of differentiating a focal injury event, which may be in need of surgical intervention, from a global event, such as swelling. In severe traumatic brain injury patients, secondary injury can develop at any time point from hours to days following the initial trauma. Stroke can behave similarly.

Prompt management of secondary injury is a clinical mainstay in improving patient prognosis. However, such injuries can vary in size, severity, location and presentation making monitoring crucial for management of intracranial trauma. Frequently, serial computed tomography scans are acquired to look for evolving intracranial pathologies. However, serial computed tomography scans leave valuable time between scans (8-24 hours), expose the patient to high-risk radiation, and the transport of such fragile patients has been shown to significantly worsen their condition.

Accordingly, a system for continuous, bedside intracranial monitoring capable of identifying focal intracranial volume changes is needed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly nor impliedly admitted as prior art against the present invention.

SUMMARY

The present disclosure relates to a system and methods for non-invasive intracranial monitoring.

According to an embodiment, the present disclosure further relates to a system for non-invasive intracranial monitoring, comprising two or more affecting electrodes arranged between a conductive location of a cranium of a patient and a location on a scalp of the patient, two or more effected electrodes arranged between the conductive location of the cranium of the patient and the location on the scalp of the patient, and processing circuitry configured to apply an electrical stimulus between the two or more affecting electrodes, measure an electrical stimulus differential between the two or more effected electrodes, calculate, for the two or more effected electrodes, a value of an impedance metric, and identify, based on the calculated value of the impedance metric, a health condition of the patient.

According to an embodiment, the present disclosure further relates to a method for non-invasive intracranial monitoring, comprising applying, by processing circuitry, an electrical stimulus between two or more affecting electrodes, the two or more affecting electrodes being arranged between a conductive location of a cranium of a patient and a location on a scalp of the patient, measuring, by the processing circuitry, an electrical stimulus differential between two or more effected electrodes, the two or more effected electrodes being arranged between the conductive location of the cranium of the patient and the location on the scalp of the patient, calculating, by the processing circuitry and for the two or more effected electrodes, a value of an impedance metric, and identifying, by processing circuitry and based on the calculated value of the impedance metric, a health condition of the patient.

According to an embodiment, the present disclosure further relates to a system for non-invasive intracranial monitoring, comprising electrodes arranged between a conductive location of a cranium of a patient and a location on a scalp of the patient, and processing circuitry configured to apply an electrical stimulus between the electrodes, measure an electrical stimulus differential between the electrodes, calculate, for the electrodes, a value of an impedance metric, and identify, based on the calculated value of the impedance metric, a health condition of the patient.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2B is a flow diagram of a method of a globally-implemented bioimpedance monitoring system, according to an exemplary embodiment of the present disclosure;

FIG. 2C is a flow diagram of an aspect of a method of a globally-implemented bioimpedance monitoring system, according to an exemplary embodiment of the present disclosure;

FIG. 4A is a flow diagram of a method of a regionally-implemented bioimpedance monitoring system, according to an exemplary embodiment of the present disclosure;

FIG. 4B is a flow diagram of an aspect of a method of a regionally-implemented bioimpedance monitoring system, according to an exemplary embodiment of the present disclosure;

FIG. 4C is a flow diagram of a method of a regionally-implemented bioimpedance monitoring system, according to an exemplary embodiment of the present disclosure;

FIG. 4D is a flow diagram of a method of a regionally-implemented bioimpedance monitoring system, according to an exemplary embodiment of the present disclosure;

DETAILED DESCRIPTION

Figure 1:
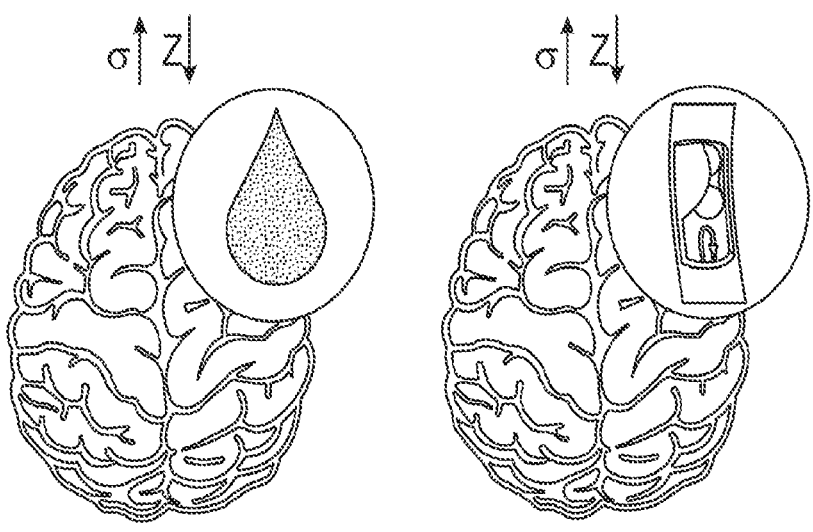
FIG. 1 is an illustration of different types of intracranial trauma in patients and their impact on electrical properties of the brain.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment". "certain embodiments", "an embodiment", "an implementation". "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Intracranial trauma is characterized by a mass effect, growth, lesion, bleeding or swelling, and can relate to pathologies including but not limited to hydrocephalus, subdural hematoma, traumatic brain injury (TBI), cerebral aneurysm, tumor and stroke. Amongst intracranial trauma, two types of injuries stand out-ischemic and hemorrhagic. Ischemic injury involves a blockage, or lack of oxygen to a designated area, while hemorrhagic involves an active bleed, or pooling of blood in the brain. Such injuries can vary in size, severity, location and presentation making monitoring (and ultimately detection) of such pathologies crucial for management of intracranial trauma patients.

Monitoring of intracranial trauma patients can either be invasive or non-invasive. In severe TBI cases the clinicians will frequently implant an intracranial pressure (ICP) monitor, usually consisting of a fiber optic probe or strain gauge transducer, into the brain to manage swelling. Management of hydrocephalus also involves placement of a pressure monitor and, ultimately, a shunt. In severe stroke patients, commonly with acute mid cerebral artery (MCA) territory stroke, an ICP monitor may be used as well to monitor their condition. Many other patients do not require invasive techniques for proper care. Computed tomography (CT) scans and magnetic resonance imaging (MRI) are the current gold-standard in intracranial visualization, and are used as the primary monitoring for less severe traumas including mild to moderate TBI, stroke, subdural hematomas and more. If a more severe injury presents, CT/MRIs may also be used in conjunction with invasive approaches.

While CT/MRIs provide powerful imaging capabilities, they present several limitations in (i) continuous patient monitoring and (ii) time to access. In the case of (i) continuous monitoring for severe TBI, it is appreciated that CT can only capture momentary snapshots of the dynamically evolving process of TBI. In this way, it has been reported that CTs can underestimate injury if within three hours of onset and may lag behind actual intracerebral damage. In severe traumas, CT scanning necessitates the patient physically leaving the intensive care unit (ICU) for a prolonged period, a risky endeavor which has been shown to exacerbate injuries and extends (ii) time to access. Moreover, intra-ICU, mobile CT scanners are not always available and often produce poor image quality. As it relates to non-radiographic approaches, MRI does not image bone well and data acquisition is lengthy, limiting its use in the ICU. Finally, serial CTs have a high cost and increase the risk of radiation induced cancer. Access to CT/MRIs can introduce (ii) a significant delay in patient care, which in less severe traumas (e.g. initial stroke diagnosis) can have significant impacts on patient prognosis. CT scans introduce a substantial time delay due to patient transport, processing, scan, diagnosis and, ultimately, treatment.

Invasive ICP monitors, while also not mobile, enable continuous monitoring; however, limitations in the ICP response have motivated investigation into more multimodal monitoring approaches to improve treatment guidance. Specifically, current ICP monitoring technology cannot distinguish between injuries arising as focal changes in intracranial volume (ICV), such as an expanding hematoma, from those arising as global changes in ICV, such as diffuse cerebral edema. Both tend to induce intracranial hypertensions, however, clinical management is vastly different depending on the etiology. For instance, onset of an injury such as a focal hematoma may require immediate surgical intervention, while generalized intracranial edema may simply be treated with osmotherapy at bedside (e.g. mannitol or hypertonic saline). Further, the probe's accuracy can "drift" over time, with resulting inaccurate measurements. Thus, it is essential to rapidly differentiate the etiology behind symptomatic intracranial hypertension. Specifically, it is imperative to identify acute traumatic mass lesions and differentiate them from diffuse injuries, as they can further exacerbate damage and may require immediate intervention. The inability of bedside ICP monitoring technology to make this distinction in real time represents an enormous disadvantage in the clinical setting.

To our knowledge, no continuous, bedside intracranial monitoring system capable of identifying focal volume changes exists. Accordingly, the present disclosure describes a bioimpedance monitoring (BIM) system capable of measuring both impedance and ICP continuously at the bedside. The mobile nature of the BIM system allows for application to, at least, severe TBI and stroke, as both injuries manifest as ischemic and hemorrhagic injuries and can be contrasted with invasive (e.g. ICP) monitoring, which may be required if treated conventionally.

Traumatic brain injury has been coined the "silent epidemic" as it is both a primary cause of death worldwide and a leading cause of disability. Approximately 2.8 million TBI related hospital encounters occur each year in the United States, alone. Of these, over 50,000 result in a fatality, with TBI killing more men 35 and younger than all other diseases combined. It's estimated that 3.2-5.3 million people in the United States are living with a TBI-related disability. In 2010, direct and indirect economic costs from TBI were estimated to be $76.5 billion, with 90% of this due to fatal TBIs or hospitalization for severe TBI. Clearly, TBI is not only a leading cause of mortality, but also a diversely damaging condition with long-reaching impacts both medically and economically.

There are two pathophysiologic phases of injury in severe TBI: primary and secondary. Primary brain injury occurs at the initial time of impact. Over the following hours to days, this damage can trigger a cascade of evolving secondary injuries which can significantly impact prognosis. Among these delayed changes are cytotoxic cerebral edema, hematoma formation or expansion, decreased brain tissue oxygen tension, tissue ischemia, and free radical generation. Secondary injuries, as they occur within the fixed, rigid vault of the skull, trigger precarious elevations in intracranial pressure (ICP). Treating elevated ICP with medical or surgical intervention mitigates the consequence of secondary injury and improves patient outcomes; as such, monitoring of ICP is the mainstay of clinical management in severe TBI.

The limitations to ICP listed above, however, present a significant challenge in management of secondary injury for TBI patients. Currently there is no ability to differentiate between global swelling and a focal infarct in need of surgical intervention. Further, there is no capability to identify the type of event happening or to localize it. As a result, secondary injury is clinically managed through serial CT scans performed every 8 to 24 hours depending on the protocol of the hospital. As discussed above, this creates delay in treatment and, thus, increased harm to the patient. Accordingly, the present disclosure describes a method for differentiating between global swelling and focal infarcts in need of surgical intervention, allowing first-responders to effectively diagnose and treat patients.

In addition to TBI, stroke stands as the 5th leading cause of death in the United States and $2^{nd}$ leading cause of death in the world. There are two primary types of stroke; ischemic and hemorrhagic. In ischemic stroke, blood clots or other fatty plaque block blood vessels to the brain starving them of oxygen. This results in neuronal inflammation and cell death within minutes. Tissue plasminogen activator (tPA) is the gold-standard for ischemic treatment and effectively dissolves the clot. However, tPA efficacy strongly correlates to timeliness of administration, with clinical benefit possible within a 4-hour treatment window. Time is so critical that the term "golden hour" refers to the first hour after stroke, the time when the most good, and bad, can be done. Hemorrhagic stroke, alternatively, occurs when a blood vessel in the brain bursts and blood spreads rather than clots, damaging surrounding tissue. While ~80% of strokes are ischemic, improper administration of tPA to a hemorrhagic stroke patient could have lethal consequences, inhibiting the natural ability of the body to limit spread of the hemorrhage. Since both stroke types result in damage to brain cells, it is critical that the stroke type be identified as soon as possible so that appropriate treatment can be administered.

Currently, the clinical standard for stroke type identification is a CT or MRI scan, both of which require patient transportation to the hospital, preparation, scheduling, and post-processing, as mentioned above. This presents many challenges for adequate stroke treatment, especially in rural areas, as patients must immediately be rushed to the hospital, and not all hospitals are equipped with specialized stroke units. The time involved in stroke management means that 72% of patients who could have benefitted from tPA never receive it. There is currently no widely available method to effectively differentiate stroke type in the field. Thus, the present disclosure describes a non-invasive method for differentiating ischemic from hemorrhagic intracranial mass effects, allowing first-responders to effectively diagnose and administer tPA on-scene.

Accordingly, the present disclosure describes a non-invasive approach to bioimpedance monitoring of the intracranial space. The corresponding bioimpedance monitoring (BIM) system allows for the detection of focal volume changes, identification of types of focal volume changes (high impedance or low impedance), and localization of the focal volume change. In this way, through detection of injury, whether hemorrhagic or ischemic, the BIM system provides the possibility to immediately alert a clinician and provide crucial treatment to patients at the time of onset.

According to an embodiment, the present disclosure relates to a system for intracranial monitoring of trauma, referred to hereinafter as a bioimpedance monitoring (BIM)

system. In an embodiment, the BIM system can be applied to a patient suspected of suffering a traumatic brain injury (TBI) and/or stroke. The purpose of the BIM system, and device thereof, is to detect a specified intracranial state. In an example, intracerebral hemorrhages and ischemic strokes may be evaluated. However, other pathologies should be considered, such as those extending beyond intracranial pressure monitoring.

According to an embodiment, the BIM system implements impedance-based metrics to compare across a multi-channel system, thereby isolating focal anomalies. This approach includes current sourcing and voltage measurement. In an embodiment, this can be accomplished via two or more electrodes, wherein one is positioned at a conductive location and the other is positioned on the scalp of the patient. In an embodiment the intracranial monitoring can be accomplished with four electrodes, two arranged at the conductive location and two arranged on the scalp of the patient. However, it can be appreciated that other arrangements and numbers of electrodes, beyond the bipolar and tetrapolar configurations described herein, may be used without deviating from the spirit of the invention.

According to an embodiment, the BIM system includes, at least, a small form-factor multi-frequency electrical impedance stimulation and acquisition module, a scalp electrode, and an electrode arranged at a conductive location(s). In an embodiment, the BIM system includes an analysis module and a display module. Though it can be appreciated that the BIM system may have a bipolar arrangement of electrodes, as will be described with respect to FIG. 4D, an exemplary embodiment of the present disclosure is implemented with a tetrapolar electrode arrangement, where two or more electrodes are arranged at the conductive location(s) and two or more electrodes are arranged on the scalp of the patient.

According to an embodiment, the BIM system of the present disclosure is a non-invasive approach. Unlike invasive approaches, with may require the use of indwelling electrodes, a non-invasive approach allows the BIM system, currently based on impedance-based measurements, to also consider the use of ultrasound, optics, or magnetic technologies in evaluate brain health to the same end as that which is described herein. As a non-invasive approach, the BIM system circumvents acknowledged challenges of ICP monitoring (i.e. high impedance boundary of the skull and poor current penetration) by identifying and exploiting additional cerebrospinal fluid access points.

The present disclosure will now be described with reference to the Figures.

Bioimpedance represents the complex electrical resistance of an organic material (e.g. tissue) to current flow, and is widely accepted as safe, low cost and easy to use in the clinical setting. Bioimpedance is sensitive to blood volume changes within tissue, as well as tissue ischemia and intracranial stroke lesions. The pathology of injury will impact the electrical properties of that tissue. For example, in an ischemic event, cells within tissue become deprived of oxygen, resulting in inflammation, a decrease in pH, cellular swelling, and cellular rupture. Each of these occurrences changes the electrical properties of that cell, and in combination, of that tissue. Similarly, in a hemorrhagic event, an active bleed with a pooling of blood or a clot is present. Blood is known to be highly conductive compared to surrounding parenchyma, thereby altering the electrical properties of that region. When compared, an ischemic event, which is shown on the right side of FIG. 1, will lower conductivity ($\sigma$) and increase impedance (Z). During a hemorrhagic event, which is shown on the left side of FIG.

1, conductivity ($\sigma$) will increase and impedance (Z) will be decreased. This gives electrical impedance the ability, as will be described in the present disclosure, to be sensitive to the intracranial pathology in a way unique to what an ICP monitor would be able to detect.

As noted above, bioimpedance represents the complex electrical resistance of an organic material (e.g. tissue) to current flow, and is widely accepted as safe, low cost and easy to use in the clinical setting. In a tetrapolar electrode arrangement of the present disclosure, current can be injected between two electrodes (I+I−) and the induced voltage can be measured between two different electrodes (V+V−). In in vivo human applications, impedance is typically measured through metallic electrodes placed on the skin around an anatomic location of interest. The electrical properties gauged are predominantly a function of the specific tissue types present (blood, white matter, bone, CSF etc.) and the tissue state (e.g. edematous vs. normally hydrated). Significant impedance differences exist between tissue types and tissue states, each of which may provide a unique mechanism for distinguishing between physiological states in clinical applications. Changing tissue states (e.g. blood pooling) will create a measurable change in impedance.

Electrical impedance spectroscopy (EIS) is the measurement of impedance at different frequencies. Cell membranes can be modeled as a parallel RC circuit. Impedance of a resistor and capacitor can be expressed as follows:

$$Z_R = R \tag{1}$$

$$Z_C = \frac{1}{jwC} \tag{2}$$

wherein $Z = R + jX$.

Due to the inherent frequency dependence (w) in the impedance of a capacitor, and the capacitive presence in the model for tissue, the electrical properties of tissue will change with frequency. Resistance of tissue is attributed to its shape, length, and resistivity which depends upon the water content of the tissue. The reactance of tissue is attributed to the capacitance of cellular membranes and signal frequency of the injected AC current. Impedance can be generalized to Ohm's Law where V is the measured electric potential and I is the injected current.

A human head is comprised of many organic materials of varying conductivities, the primary of which being skull, skin, CSF, fat, gray matter and white matter. It is appreciated that the high impedance barrier of the skull has made systems, such as that described herein, historically difficult. For instance, it is incredibly difficult for current to penetrate through the bone of the skull, thus severely limiting the ability of a system to sense pathologic changes or injuries. In solving this problem, it is important to note CSF is 100× more conductive than the bone of the skull and it surrounds the entire brain. Therefore, by exploiting the CSF, it is possible to provide current to the brain while circumnavigating the dense skull surrounding it. Thus, a non-invasive method of intracranial measurement, as described herein with reference to the BIM system, has the potential to impact patients beyond traumatic brain injury (TBI) or stroke.

According to an embodiment of the present disclosure, the BIM system exploits specific anatomical landmarks that are proximal to CSF channels, the CSF being a highly conductive (~2.0 S/m) substance surrounding the whole brain. These specific anatomical landmarks include the cochlear tract, the orbits, the soft palate and the skull base. In an example, the specific anatomical landmarks may include either of the orbits and the soft palate.

In an embodiment, the BIM system is designed in view of the following criteria: 80 dB SNR, 99% accuracy, 100 kHz frequency bandwidth, and multi-channel. Moreover, the BIM system was designed to be compatible with CT, the current gold-standard for imaging in TBI. Additional design criteria are described in Table 1.

TABLE 1

| OBJECTIVES | DESIGN REQUIREMENTS | DESIGN STRATEGY AND ACCEPTANCE CRITERION |
|---|---|---|
| (1) Ability to measure small volumes in | High signal-to-noise ratio (SNR) | SNR >= 80 dB Voltage controlled current source to reduce noise on input power |
| high noise environment (i.e. ICU) | Variable frequency | 100 kHz bandwidth Tetrapolar |
| | Small volume changes for induced injury Robust electronics | High precision linear stage volume control (.001 uL/min) High input Z amplifiers (CMR above 90 dB at unity gain) Low voltage drift (<25 uV/° C.) |
| (2) Ability to detect a focal vs global injury | Multi-sector resolution | 8 channels Minimum 16 channel capability (two mux) |
| (3) Ability to differentiate event type | High accuracy | Accuracy >=99% High precision low noise IAs Matched filter for voltage sense |
| | High impedance and low impedance models | Autologous blood injection Fogarty balloon inflation |
| (4) Ability to implement system in a validating surgical environment | Intracranial imaging compatibility (computed tomography) No additional trauma to 'patient' | Fit within bore of a CT scanner Ag/AgCl tab electrodes Polypropylene cranial bolts ICP coupled to internal electrodes (patented design) Biocompatible |
| | Physiologic monitoring (?) | Biopac vitals Blood gasses |

The BIM system was designed based on the tetrapolar electrode measurement configuration described above in order to provide broadband impedance acquisition and maximize sensitivity. Two drive electrodes inject current ($I^+$ and $I^-$) using a Howland-based voltage-controlled current source and two pick-up electrodes measure the induced potential ($V^+$ and $V^-$), as shown in FIG. 2. In the event current is applied to the patient, the drive electrodes can be referred to as affecting electrodes and the pick-up electrodes can be referred to as effected electrodes. Of course, in the event a voltage differential is applied to the patient, the affecting electrodes may be V+ and V− while the effected electrodes may be I+ and I−.

Figure 2A:
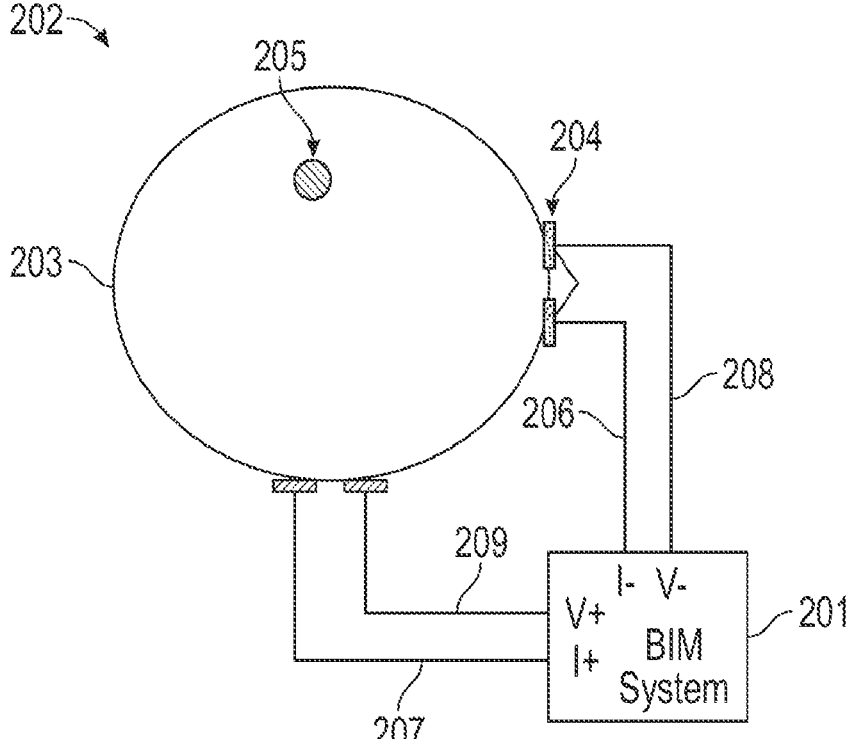
FIG. 2A is an illustration of a globally-implemented bioimpedance monitoring system, according to an exemplary embodiment of the present disclosure.

Having described design parameters of the BIM system, the BIM system will be considered in view of FIG. 2A, wherein a BIM system 201 can be used to determine the presence of and type of an intracranial event.

In an embodiment, it may be desirable for an emergency responder to be able to determine, in real-time, whether a patient suffering an intracranial trauma has experienced an ischemic event or a hemorrhagic event. As shown in FIG. 2A, the intracranial event may be a trauma, or mass effect 205, within a head 203 of a patient 202. The BIM system 201 may include electrodes in electrical contact with a conductive location(s) 204 on the head 203 of the patient 202 and electrodes in electrical contact with a scalp of the patient 202. In an example, the electrodes in electrical contact with the conductive location(s) 204 may be, in the event a voltage-controlled current is applied to the head 203 of the patient 202 by the BIM system 201, an affecting electrode 206 and an effected electrode 208. In the example, the conductive location(s) 204 may be the orbits of the patient 202 and the affecting electrode 206 and the effected electrode 208 may be in proximate tear ducts of the eyes. Moreover, the electrodes in electrical contact with the scalp of the patient 202 may be, in the event the voltage-controlled current is applied to the head 203 of the patient 202 by the BIM system 201, an affecting electrode 207 and an effected electrode 209. The position of the affecting electrode 207 and the effected electrode 209 on the scalp of the patient 202 may be arbitrary and may be repositionable. With the BIM system 201 in position on the head 203 of the patient 202, an electrical stimulus, or the voltage-controlled current, can be applied to the head 203 of the patient 202 and the resulting electrical stimulus differential, or voltage differential, can be measured in order to calculate a value of an impedance metric of the head 203 of the patient 202. As the emergency responder needs to determine, in real-time, the health condition of the patient 202, certain biometric parameters of the patient 202 may be used to obtain reference values of an impedance metric that can be used as a comparison. By using the reference values, a probable health condition of the patient can be evaluated and it can be immediately determined if certain care needs to be administered. For instance, in the event the mass effect 205 is a blockage, the value of the impedance metric may indicate a relative increase in impedance within the brain tissue, indicating a likely ischemic event, and tissue plasminogen activator (tPA) can be administered in order dissolve the blockage and restore oxygen to the effected brain tissue.

The illustration of FIG. 2A will now be described with reference to the flow diagrams of FIG. 2B and FIG. 2C.

Figure 9A:
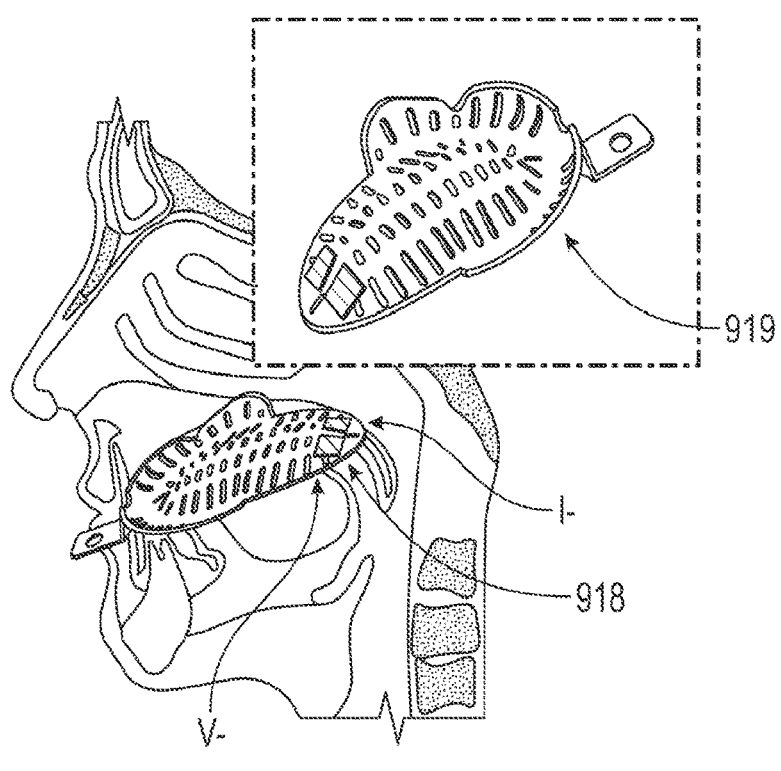
FIG. 9A is an illustration of a device including an affecting electrode and an effected electrode, the device being arranged at a conductive location of the patient, according to an exemplary embodiment of the present disclosure.
Figure 9B:
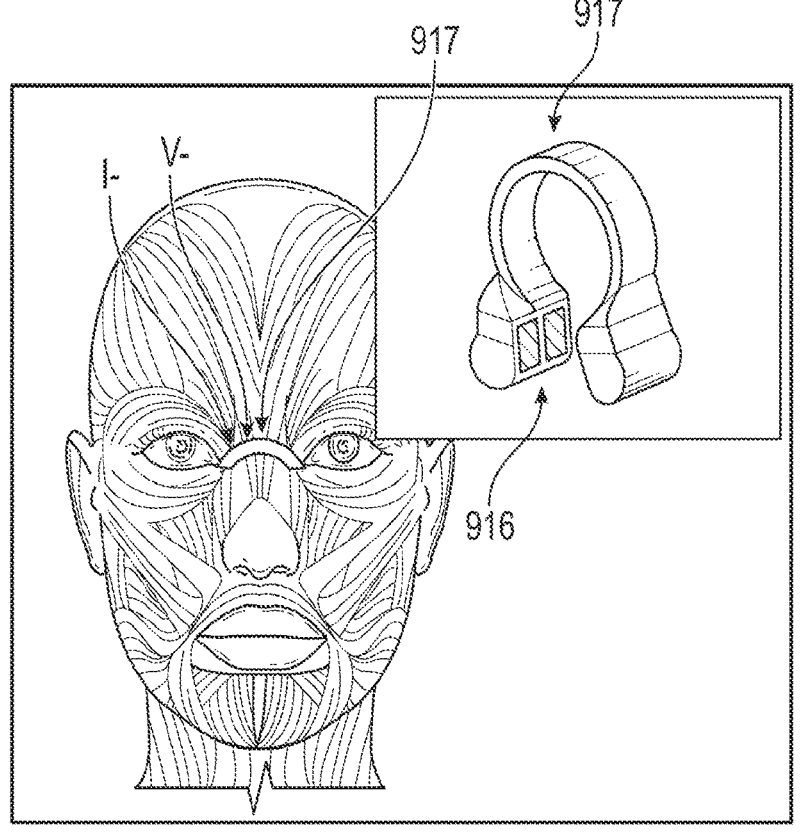
FIG. 9B is an illustration of a device including an affecting electrode and an effected electrode, the device being arranged at a conductive location of the patient, according to an exemplary embodiment of the present disclosure.

Method 210 describes a technique for evaluating, globally, a health condition of a patient. Method 210 is described from a point at which, for instance, an emergency responder as arrived to a patient having an intracranial event and has attached the BIM system to the patient. Though the BIM system will be described in more detail with reference to subsequent Figures, it can be appreciated that the BIM system can include the electrical simulation source and the electrodes required to provide electrical contact to the head of the patient. Software controlling the BIM system can be envisioned within a mobile friendly application package that can be executed within a mobile device for electrical stimulation and analysis of the health condition of the patient at the point of care. In an example, electrical contact with the conductive location of the head can be a nasal bridge device that provides electrical contact with the orbits of the patient, as illustrated in FIG. 9B. In an example, electrodes on the scalp of the patient can be silicone tab electrodes mounted side by side with ~2.5 mm spacing and the silicone tab electrodes can be secured with electrode paste.

At step 220 of method 210, the electrical stimulus can be provided between an affecting electrode located at the conductive location and an affecting electrode located on the scalp of the patient. The electrical stimulus may be a voltage differential or an injected current. In an example, the electrical stimulus is an injected current provided by a Howland voltage-controlled current source (VCCS) of the BIM system. The VCCS of the BIM system may provide a current to the head of the patient over a range of between 0.5 mA and 5.0 mA. In an example, the VCCS of the BIM system may provide a 2.3 mA sinusoidal current at 40 kHz to the head of the patient.

At step 222 of method 210, a differential between an effected electrode at the conductive location and an effected electrode located on the scalp of the patient can be measured. In an embodiment, both current and voltage can be sampled from at 50 kHz and the amplitudes extracted using a matched filter.

At step 224 of method 210, the differential between the effected electrode at the conductive location and the effected electrode located on the scalp of the patient can be used to determine a value of an impedance metric of the head of the patient. In an embodiment, impedances can be determined from the differential, or as a ratio of voltage to current at a rate of 50 Hz, averaging of 1000 samples per data point.

At step 230 of method 210, the calculated value of the impedance metric of the head of the patient can be used to identify a health condition of a patient.

For instance, as illustrated in the flow diagram of FIG. 2C, method 210 may further comprise, at step 226, determining a differential between the value of the impedance metric of the head of the patient and a reference value of a reference impedance metric obtained from a database of reference impedance values 228. The reference value of the reference impedance metric may be based on certain biometrics of the patient (e.g. age, sex, weight, BMI, height, etc.) and may represent a baseline from which the determined value of the impedance metric of the patient, determined in real-time, can be given context and compared.

Accordingly, at step 230 of method 210, the health condition of the patient can be identified. For instance, if it is determined that the value of the impedance metric of the patient is decreased relative to the baseline obtained from the reference value of the reference impedance metric, then it is probable that the patient is experiencing a hemorrhagic event. The determination of the decrease in the value of the impedance metric may be based on a comparison to the baseline relative to a threshold percent error from the baseline or may be based on a magnitude of the discrepancy from the baseline. In another instance, if it is determined that the value of the impedance metric of the patient is elevated relative to the baseline obtained from the reference value of the reference impedance metric, then it is probable that the patient is experiencing an ischemic event. The determination of the increase in the value of the impedance metric may be based on a comparison to the baseline relative to a threshold percent error from the baseline or may be based on a magnitude of the discrepancy from the baseline. Of course, in an ideal situation, any change in the value of the imped- ance metric of the head of the patient is insufficient to satisfy the above requirements for identification as an ischemic event, a hemorrhagic event, or other pathological event. In this situation, it can be determined it is probable the patient is not suffering one of these events.

At step 232 of method 210, a notification may be generated based on the health condition identified at step 230 of method 210. For instance, if the patient is identified as having a hemorrhagic event, a notification may be transmitted to the mobile device of the emergency responder and to medical infrastructure systems or nearby hospitals so that care can be coordinated. In the instance the patient is identified as having an ischemic event, a notification can, similarly, be transmitted to the mobile device of the emergency responder and to medical infrastructure systems or nearby hospitals in order to coordinate. However, in the event the patient is identify as being ischemic, the emergency responder may be equipped to respond in real-time, which is shown to be critical (see above description of golden hour). To this end, if the generated notification indicates it is probable the patient is suffering an ischemic event, the emergency responder may supply the patient with tPA in order to dissolve the blockage and restore oxygenation to the brain tissue.

In an embodiment, the notification may be a visual alert on a display of the mobile device, an audible alert via speakers of the mobile device, or a haptic alert via a vibration system of the mobile device. In an example, the generated notification may include an automatic dialing service that rings a nearby hospital center, allowing the emergency responder to immediately notify nearby medical providers of the type of care that will be needed. An exemplary mobile device will be described with reference to FIG. 10.

Figure 3A:
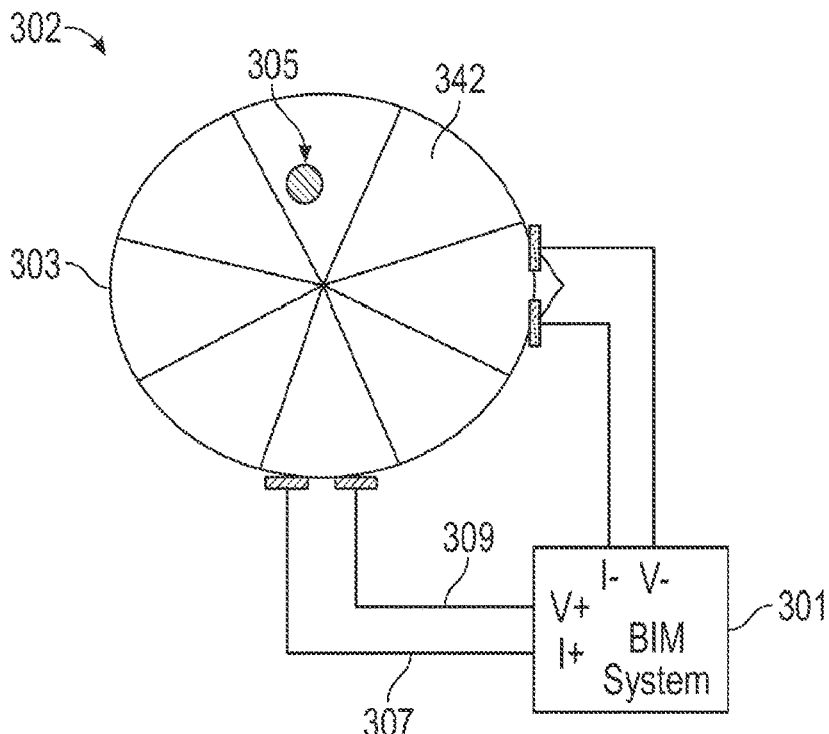
FIG. 3A is an illustration of a regionally-implemented bioimpedance monitoring system, according to an exemplary embodiment of the present disclosure.

Of course, not all implementations of the BIM system are in the field and performed by emergency responders on the scene. In certain instances, a patient may require a more detailed, focal evaluation. Though the global implementation of the BIM system of FIG. 2A through FIG. 2C is useful in emergency scenarios, it is unlikely to be able to pin point a location of the mass effect with the use of only a single set of scalp electrodes. Such an instance is illustrated in FIG. 3A. Even if a head 303 of a patient 302 is considered to have regions 342, a mass effect 305 is unlikely to be detected if a BIM system 301 only has access to a single set of electrodes 307, 309 positioned on a scalp of the head 303 of the patient 302.

Figure 3B:
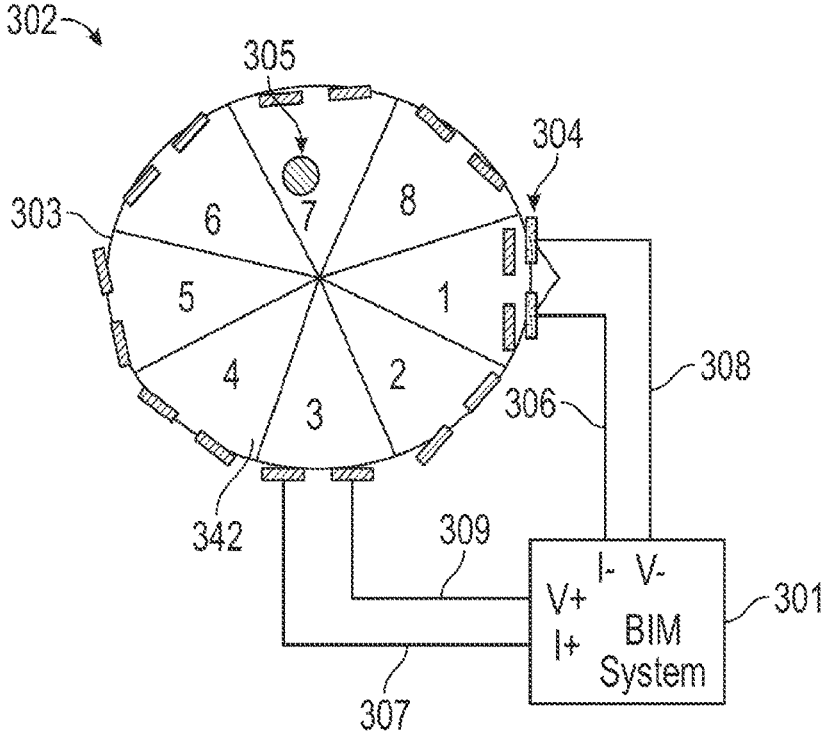
FIG. 3B is an illustration of a regionally-implemented bioimpedance monitoring system, according to an exemplary embodiment of the present disclosure.

In order to be able to provide a focal health condition of the patient, the BIM system may be outfitted with additional sets of scalp electrodes, as shown in FIG. 3B. Though not shown with connecting wires in FIG. 3B, for clarity, it can be appreciated that a head 303 of a patient 302 may be outfitted with, for each enumerated region 342 of the head 303 of the patient 302, an affecting electrode 307 and an effected electrode 309. In this way, and in conjunction with an affecting electrode 308 and an effected electrode 306 in electrical contact with a conductive location(s) 304 of the head 303 of the patient 302, a BIM system 301 can provide electrical stimulus, measure differentials, and calculate regional impedance values for each region 342 of the head 303 of the patient 302 in order to identify a location of a mass effect 305.

FIG. 4A through FIG. 4D are flow diagrams of a regional implementation of the BIM system in order to determine a focal health condition of a patient. The illustration of FIG. 3B can be referenced throughout.

Method 440 describes a technique for evaluating, regionally, a health condition of a patient. Method 440 is described from a point at which, for instance, a patient has already been admitted to a hospital and non-invasive evaluation of a specific location of a mass effect of the patient is desired. In an embodiment, the BIM system can be outfitted to the patient when the patient is under medical examination and can remain outfitted during the patient's stay in the hospital. In this way, regional evaluation (and global evaluation) of the brain of the patient can be performed automatically and iteratively and hospital staff can be alerted without need for continuous oversight.

Though the BIM system will be described in more detail with reference to subsequent Figures, it can be appreciated that the BIM system can include the electrical simulation source and the electrodes required to provide electrical contact to the head of the patient. As in FIG. 3B, the electrodes may be a set of electrodes placed at a conductive location on the head of the patient (i.e., the orbits) and a plurality of sets of electrodes placed around the head of the patient in positions corresponding to enumerated regions of the brain. Software controlling the BIM system can be envisioned within a mobile friendly application package that can be executed within a mobile workstation for electrical stimulation and analysis of the focal health condition of the patient at bedside. In an example, electrical contact with the conductive location of the head can be a nasal bridge device that provides electrical contact with the orbits of the patient, as illustrated in FIG. 9B. In another example, electrical contact with the conductive location of the head can be an oral device that provides electrical contact with the soft palate of the patient. The electrodes on the scalp of the patient can be silicone tab electrodes mounted side by side with ~2.5 mm spacing and the silicone tab electrodes can be secured with electrode paste.

At step 450 of method 440 of FIG. 4A, the electrical stimulus can be provided between an affecting electrode located at the conductive location and an affecting electrode associated with a first region of the brain on the scalp of the patient. The electrical stimulus may be a voltage differential or an injected current. In an example, the electrical stimulus is an injected current provided by a Howland voltage-controlled current source (VCCS) of the BIM system. The VCCS of the BIM system may provide a current to the first region of the brain of the patient over a range of between 0.5 mA and 5.0 mA. In an example, the VCCS of the BIM system may provide a 2.3 mA sinusoidal current at 40 kHz to the first region of the brain of the patient.

At step 452 of method 440, a differential between an effected electrode at the conductive location and an effected electrode associated with the first region of the brain on the scalp of the patient can be measured. In an embodiment, both current and voltage can be sampled from at 50 kHz and the amplitudes extracted using a matched filter.

At step 454 of method 440, the differential between the effected electrode at the conductive location and the effected electrode associated with the first region of the brain on the scalp of the patient can be used to determine a value of a regional impedance metric of the head of the patient. In an embodiment, impedances can be determined from the differential, or as a ratio of voltage to current at a rate of 50 Hz, averaging of 1000 samples per data point.

At step 460 of method 440, the calculated value of the regional impedance metric of the first region of the brain of the patient can be used to identify a focal health condition of a patient.

For instance, as illustrated in the flow diagram of FIG. 4B, method 440 may further comprise, at step 456, determining a differential between the value of the regional impedance metric of the first region of the brain of the patient and a reference value of a reference regional impedance metric obtained from a database of reference regional impedance values 228. The reference value of the reference regional impedance metric may be based on certain biometrics of the patient (e.g. age, sex, weight, BMI, height, etc.) and may represent a baseline from which the determined value of the reference impedance metric of the patient, determined in real-time, can be given context and compared.

Accordingly, at step 460 of method 440, the focal health condition of the patient can be identified. For instance, if it is determined that the value of the regional impedance metric of the patient is decreased relative to the baseline obtained from the reference value of the reference regional impedance metric, then it is probable that the patient is experiencing a hemorrhagic event within the first region of the brain. The determination of the decrease in the value of the regional impedance metric may be based on a comparison to the baseline relative to a threshold percent error from the baseline or may be based on a magnitude of the discrepancy from the baseline. In another instance, if it is determined that the value of the regional impedance metric of the patient is elevated relative to the baseline obtained from the reference value of the reference regional impedance metric, then it is probable that the patient is experiencing an ischemic event. The determination of the increase in the value of the regional impedance metric may be based on a comparison to the baseline relative to a threshold percent error from the baseline or may be based on a magnitude of the discrepancy from the baseline. Of course, in an ideal situation, any change in the value of the regional impedance metric of the first region of the brain of the patient is insufficient to satisfy the above requirements for identification as a regional ischemic event, a regional hemorrhagic event, or other pathological event. In this situation, it can be determined it is probable the patient is not suffering one of these events in the first region of the brain.

At step 462 of method 440, a notification may be generated based on the focal health condition identified at step 460 of method 440. For instance, if the patient is identified as having a hemorrhagic event in the first region of the brain, a notification may be transmitted to medical infrastructure systems to alert physicians and nurses and to coordinate patient care. As the analysis and evaluation of the BIM system can be conducted iteratively, automatically, and in real time, the notification can allow care to be provided directly without need for constant oversight. In the instance the patient is identified as having a regional ischemic event, a notification can, similarly, be transmitted to medical infrastructure systems to alert physicians and nurses and to coordinate patient care. If a regional ischemic event is detected, an attending nurse or physician may provide tPA, for example, to dissolve the blockage and restore tissue oxygenation. In another example, the administration of the tPA, or other appropriate medication, can be automated in response to detecting a probable regional ischemic event.

In order to evaluate each region of the brain of the patient, process 440 may be performed iteratively and successively for each region of the brain of the patient.

In an embodiment, a database of reference values of reference regional impedance metrics is not available or is not appropriate. In this case, electrical stimuli can be applied to electrodes corresponding to two or more regions of the brain of the patient and relative comparisons can be made to determine the condition of a specific region of the patient.

To this end, and having determined a value of a first regional impedance metric, a value of a second regional impedance metric can be determined, as will be described with reference to FIG. 4C.

At step 451 of method 440, an electrical stimulus can be provided between the affecting electrode located at the conductive location and an affecting electrode associated with a subsequent, or second, region of the brain on the scalp of the patient. The electrical stimulus may be a voltage differential or an injected current. In an example, the electrical stimulus is the same as that applied to the first region of the brain of the patient and is an injected current provided by a Howland VCCS of the BIM system. The VCCS of the BIM system may provide a current to the second region of the brain of the patient over a range of between 0.5 mA and 5.0 mA. In an example, the VCCS of the BIM system may provide a 2.3 mA sinusoidal current at 40 kHz to the second region of the brain of the patient.

At step 453 of method 440, a differential between an effected electrode at the conductive location and an effected electrode associated with the second region of the brain on the scalp of the patient can be measured. In an embodiment, both current and voltage can be sampled from at 50 kHz and the amplitudes extracted using a matched filter.

At step 455 of method 440, the differential between the effected electrode at the conductive location and the effected electrode associated with the second region of the brain on the scalp of the patient can be used to determine a value of a regional impedance metric of the head of the patient. In an embodiment, impedances can be determined from the differential, or as a ratio of voltage to current at a rate of 50 Hz, averaging of 1000 samples per data point.

In order to determine relative characteristics of the regions of the brain of the patient, the value of the first regional impedance metric and the value of the second regional impedance metric can be compared at step 457 of method 440.

The comparison at step 457 of method 440 may be performed much in the same way the previous comparisons, to reference values, was performed. If, for instance, the impedance of the first region of the brain is higher than the impedance of the second region of the brain, this would indicate that one or the other of the brain is exhibiting a mass effect of some type.

Of course, method 440 of FIG. 4C can be performed iteratively until all regions of the brain have been evaluated. Individual comparisons between a first region of the brain and a second region of the brain can be compared, and collective comparisons between multiple regions of the brain can be performed to identify any abnormalities that exist. By collectively evaluating the impedance values of the regions of the brain, it can be determined whether a first region was abnormally elevated or abnormally reduced relative to a second region.

In this way, the differential focal health condition of the patient can be identified at step 459 of method 440. This differential focal health condition of the patient can indicate that a mass affect is located in a certain region of the brain. In this instant the mass effect has led to an increase in impedance in that certain region of the brain, appropriate medication can be provided to restore oxygenation to the ischemic tissue.

It can be appreciated that the comparison of step 457 of method 440 appears to be an instantaneous evaluation. In certain cases, the comparison can be performed in based on data being received a given instant or averaged over a period of, for instance, 10 seconds. In another embodiment, the comparison can be performed using data collected over a longer duration and can include an evaluation of rates of change of metrics of the patient.

For instance, the evaluation could include calculating a first derivative of data received from each region of the brain, comparing the first derivatives associated with each region of the brain, and identifying an outlier. In an example, the outlier could be identified based on the rate of change in that region of the brain being 3 standard deviations from the mean. In another example, the outlier could based on an $R^2$ fit.

In another instance, the evaluation could be based on an SEAIC change, over time, for each electrode associated with a region of the brain. The valuation could include identifying an outlier amongst the electrodes on the scalp of the patient.

In another instance, the evaluation could include calculating a second derivative of data received from each region of the brain, comparing the second derivatives associated with each region of the brain, and identifying an outlier. In an example, the outlier could be identified based on the rate of change in that region of the brain accelerating more than 5% of the prior change.

According to an embodiment, the comparison of step 457 of method 440 of FIG. 4C can include a ratiometric analysis, or a determination of an asymmetric index that compares, in an example, impedance values of hemispheres of the brain. To this end, the scalp electrodes can be placed along a single plane determined in accordance with which configurations minimized conductivity asymmetry between hemispheres. The lateral asymmetry index can calculated for the electrodes situated at four different vertical planes (parallel to axial plane) with two different spacing configurations between adjacent electrodes at each plane (eight total scalp placement arrangements). Accordingly the asymmetry Index (AI) between the hemispheres can be calculated with the following equation and minimized:

$$AI = \frac{Z_{left} - Z_{right}}{Z_{left} + Z_{right}} * 100$$

where $Z_{left}$ and $Z_{right}$ represent impedance of the left hemisphere and the right hemisphere, respectively.

The impedance of the left hemisphere and the right hemisphere can be determined by, in an example, calculating the mean of the sink electrode averaging impedance change (SEAIC) of lateral electrodes of hemisphere. The SEAIC can be calculated by holding the sink (I—) electrode fixed and considering all patterns which use that electrode as a sink electrode. These patterns could then be averaged to obtain the SEAIC. Alternatively, the considered patterns can be fit to a distribution and their variance pulled out, or the first quartile range collected and averaged (etc. . . . ) to provide a single number associated with that electrode position.

In an embodiment, predicted stroke location can be assigned by the scalp electrode with the highest SEAIC. Stroke type can be categorized in accordance with SEAICs. For a given injury condition, the following formula can be applied:

$$(\max(SEAIC) - \min(SEAIC)) = \begin{cases} x < 0 & \text{hemorrhagic} \\ x \geq 0 & \text{ischemic} \end{cases}$$

Though the above-described asymmetry index is a ratiometric indicator, it could also be a differential indicator between left hemisphere and right hemisphere, a leave-one-out indicator (e.g., average 11/12 electrodes and divide by the $12^{th}$, rotate which was left out, and identify the largest difference between regions), a variance based indicator (e.g., calculated variance across all electrode channels as its own asymmetry index), a range-based indicator (e.g., look at the spread across all channels, and then between regions, to identify regional anomalies), and the like.

With reference to FIG. 4D, method 440 will be described in another implementation.

At step 470 of method 440 of FIG. 4D, the electrical stimulus can be provided between an affecting electrode located at the conductive location and an affecting electrode associated with a first region of the brain on the scalp of the patient. The electrical stimulus may be a voltage differential or an injected current. In an example, the electrical stimulus is an injected current provided by a Howland voltage-controlled current source (VCCS) of the BIM system. The VCCS of the BIM system may provide a current to the first region of the brain of the patient over a range of between 0.5 mA and 5.0 mA. In an example, the VCCS of the BIM system may provide a 2.3 mA sinusoidal current at 40 kHz to the first region of the brain of the patient.

As above, a differential between an effected electrode at the conductive location and an effected electrode associated with the first region of the brain of the patient can be measured. In an embodiment, both current and voltage can be sampled from at 50 kHz and the amplitudes extracted using a matched filter.

However, as at step 472 of method 440 of FIG. 4D, a differential may be measured between an effected electrode associated with the first region of the brain of the patient and an effected electrode associated with a second region of the brain of the patient, the effected electrode of the second region of the brain not being electrically stimulated by the current applied at step 470 of method 440.

At step 474 of method 440, the differential between the effected electrode associated with the first region of the brain of the patient and the effected electrode associated with the second region of the brain of the patient can be used to determine a value of an inter-regional impedance metric of the head of the patient. In an embodiment, impedances can be determined from the differential, or as a ratio of voltage to current at a rate of 50 Hz, averaging of 1000 samples per data point.

At step 476 of method 440, the calculated value of the inter-regional impedance metric of the brain of the patient can be used to identify a focal health condition of a patient.

Figure 5A:
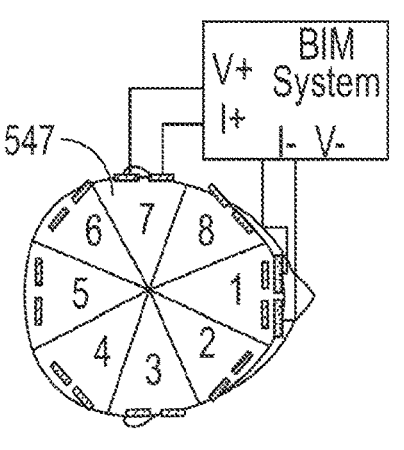
FIG. 5A is an illustration of a regionally-implemented bioimpedance monitoring system, according to an exemplary embodiment of the present disclosure.
Figure 5B:
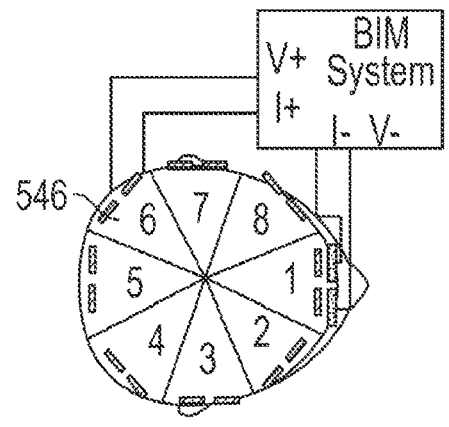
FIG. 5B is an illustration of a regionally-implemented bioimpedance monitoring system, according to an exemplary embodiment of the present disclosure.
Figure 5C:
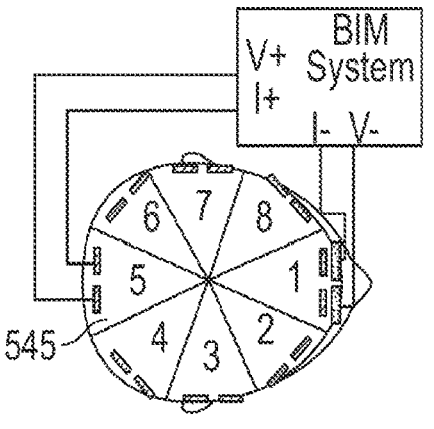
FIG. 5C is an illustration of a regionally-implemented bioimpedance monitoring system, according to an exemplary embodiment of the present disclosure.
Figure 5D:
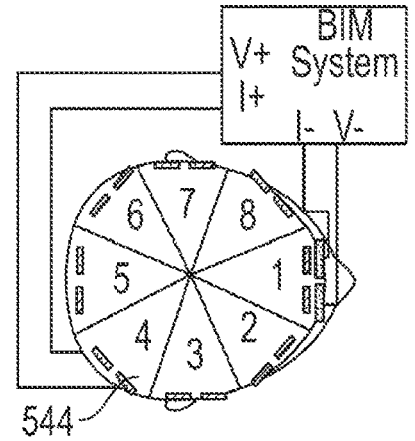
FIG. 5D is an illustration of a regionally-implemented bioimpedance monitoring system, according to an exemplary embodiment of the present disclosure.

Method 440 described above can be visually appreciated with respect to FIG. 5A through FIG. 5D. As can be seen in FIG. 5A, and in view of FIG. 4A and FIG. 4B, an electrical stimulus may be applied between electrodes arranged at the orbits of the patient and electrodes associated with a seventh region 547 of the brain of the patient. With just this, an intraregional comparison can be performed in view of reference regional impedance values and in view of changes in the regional impedance value with time. Of course, with reference to FIG. 5B through FIG. 5D, and in view of FIG. 4C and FIG. 5A, electrical stimulation may be successively and iteratively applied to additional regions of the brain to continuously monitor and evaluate focal health of the brain of the patient. By applying electrical stimuli to a sixth region 546 of the brain, a fifth region 545 of the brain, and a fourth region 544 of the brain in FIG. 5B, FIG. 5C, and FIG. 5D, respectively, it is possible perform instant or longitudinal ratiometric analyses, inter-regional analyses, and eliminate the need for reference regional impedance values.

Figure 6:
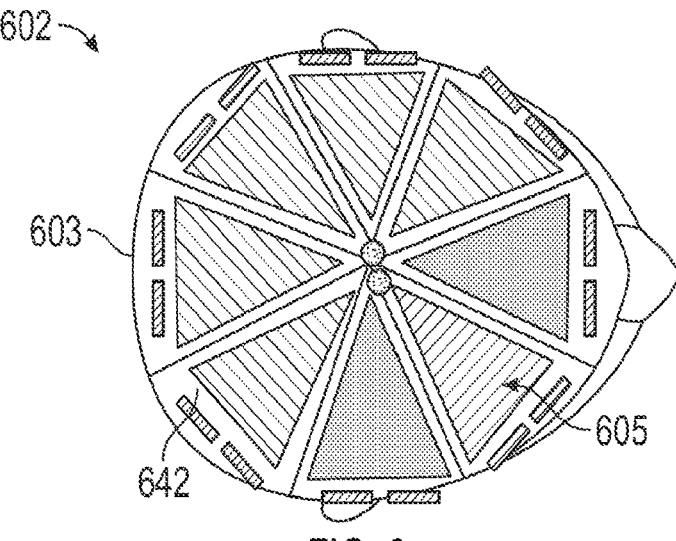
FIG. 6 is an illustration of visual display used in accordance with a regionally-implemented bioimpedance monitoring system, according to an exemplary embodiment of the present disclosure.

FIG. 6 is an illustration of a focal map that may be generated and displayed via a display of a BIM system computing device. The focal map reflects evaluations of the regions of the brain performed according to the methods described herein and shown in FIG. 5A through FIG. 5D. The notification generated at step 462 of method 440 may be an illustration of a head 603 of a patient 602 detailing which region 642 of the brain is experiencing a focal event. As in FIG. 6, a mass effect 605 may be located in the front of the left hemisphere of the brain, as indicated by a striped region of the brain, which neighboring regions reflecting their proximity.

Figure 7:
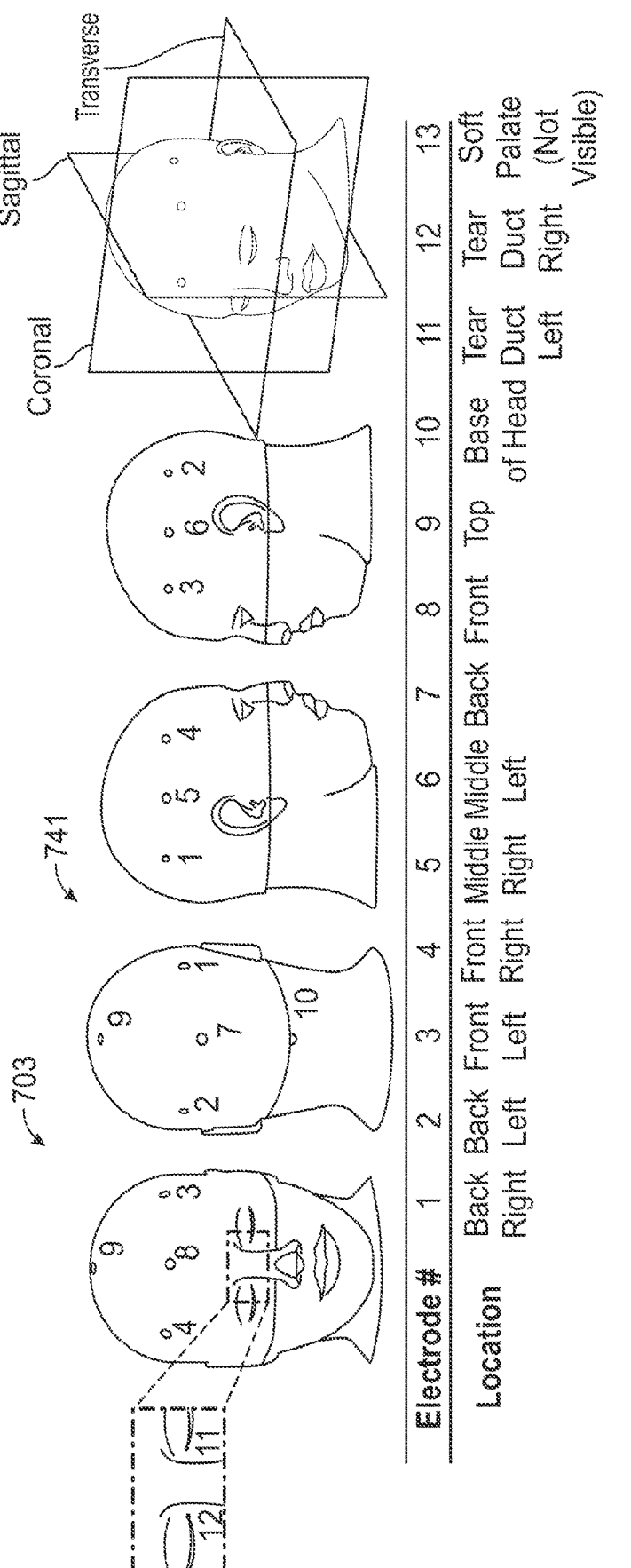
FIG. 7 is an illustration of electrode placements of a patient within a regionally-implemented bioimpedance monitoring system, according to an embodiment of the present disclosure.

According to the embodiment described above, the BIM system may include a plurality scalp electrodes. Each of these electrodes may occupy a scalp electrode position 741 around a head 703 of a patient, as shown in FIG. 7. Electrode positions 10-13 indicate conductive regions of the head that can be used to perturb the brain via the CSF. In an embodiment, electrode position 9 is optional, the regions of the brain being adequately evaluated by electrode positions 1-8.

Figure 8:
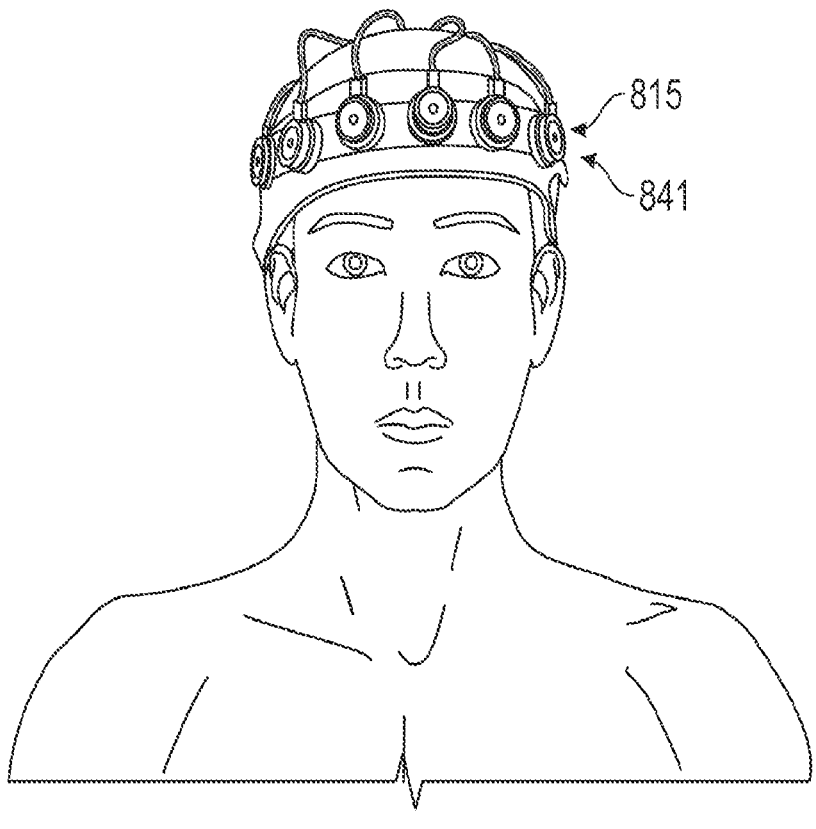
FIG. 8 is an illustration of an electrode garment arranged on a scalp of a patient within a regionally-implemented bioimpedance monitoring system, according to an embodiment of the present disclosure.

FIG. 8 provides an image of an electrode garment of the BIM system, according to an exemplary embodiment of the present disclosure. A head covering 815 including a plurality of electrodes is shown on a head of a patient, the head covering 815 including the plurality of electrodes at specific scalp electrode positions 841. The head covering 815 can be in electrical communication with computing hardware of the BIM system in order to, in coordination with electrodes arranged at conductive locations, receive and transmit electrical stimuli to and from the brain of the patient. In an embodiment, the scalp electrodes consist of silicon tab electrodes mounted side by side with 2 mm to 3 mm spacing. The silicon tab electrodes may be 7 mm diameter electrodes (Kendall EK310). The electrodes cast minimal CT artifacts and will enable us to obtain continuous CT scans during the simulated strokes.

As it relates to the conductive locations described above, FIG. 9A and FIG. 9B provide illustrations of electrode-based devices designed to contact various conductive locations of the patient. The conductive locations were identified as areas proximal to CSF and potentially presenting low impedance "windows" into the intracranial space. In particular, the orbits, the soft palate, the cochlear tract, and the base of the skull were identified. For instance, with regard to a soft palate device 919 shown in FIG. 9A, two Ag/AgCl electrodes 918 may be embedded on a distal end of a tongue depressor shaped instrument capable of traversing the mouth of a patient. An electrode harness can be configured to connect all electrodes directly to a data acquisition module of the BIM system. With regard to the orbits, and as shown in FIG. 9B, orbit electrodes 916 may be implemented by the bridge of the nose with electrodes touching the inner corners of each eye proximate tear ducts of the eyes. The orbit access device 917 minimizes impact to the patient, eliminating the need to close eyelids or tape the eyelids shut and is non-interfering with other monitors typically used in an ICU setting.

Figure 10:
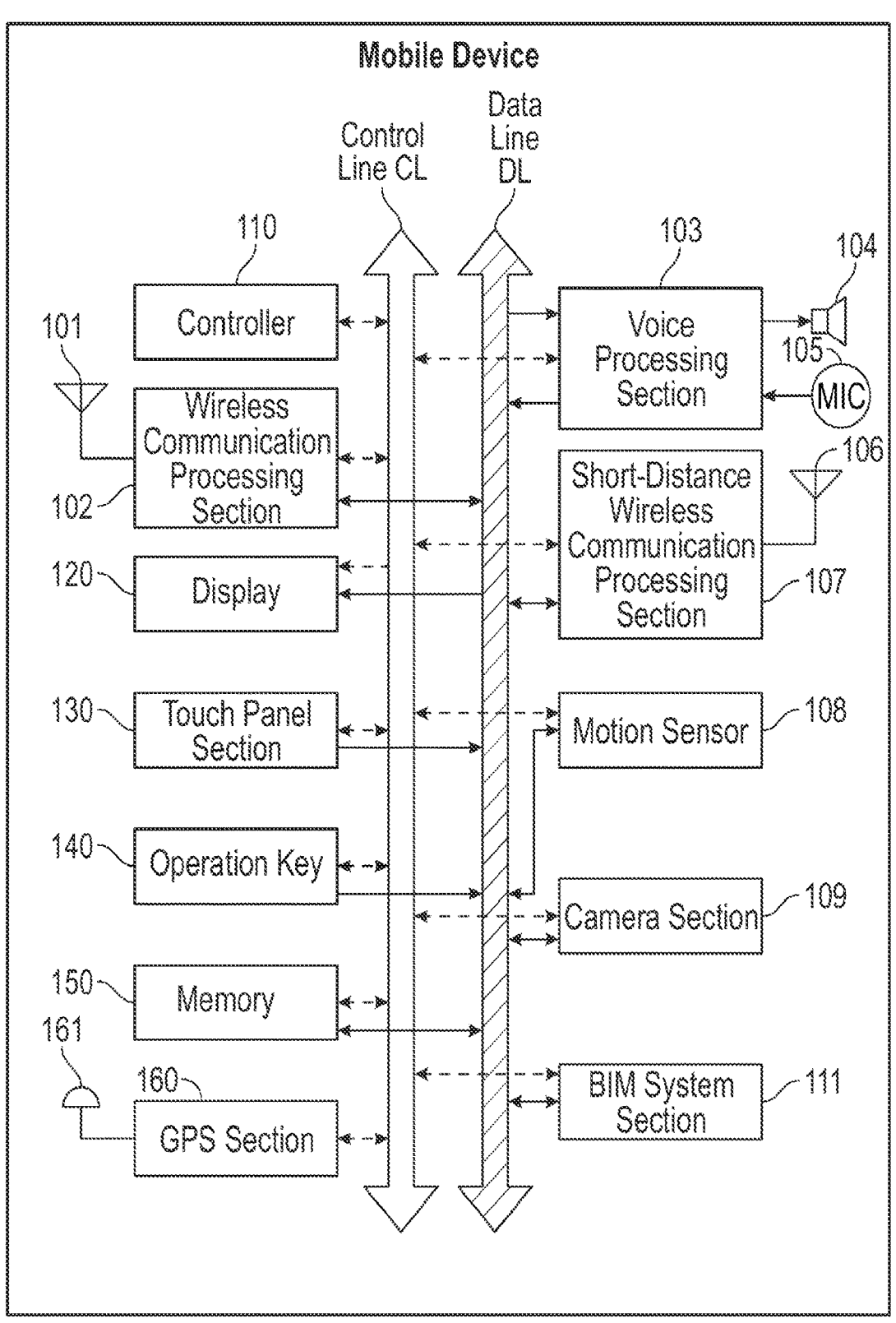
FIG. 10 is a hardware diagram of a mobile device that can be used at a point-of-care in conjunction with a bioimpedance monitoring system, according to an exemplary embodiment of the present disclosure.

FIG. 10 is a more detailed block diagram illustrating an exemplary mobile device 20, according to certain embodiments of the present disclosure. In certain embodiments, such as those described with reference to FIG. 2A through FIG. 2C, the mobile device 20 may be a smartphone. However, the skilled artisan will appreciate that the features described herein may be adapted to be implemented on other devices (e.g., a laptop, a tablet, a server, an e-reader, a camera, a navigation device, etc.) that can be mobile and can be made available in appropriate situations. Alternatively relevant processing steps, including notification generation, need not be performed on the mobile device 20, but can be performed remotely and then executed, via a display, speakers, and the like, by the mobile device 20. The exemplary mobile device 20 of FIG. 10 includes a controller 110 and a wireless communication processor 102 connected to an antenna 101. A speaker 104 and a microphone 105 are connected to a voice processor 103.

The controller 110 may include one or more Central Processing Units (CPUs) and may control each element in the mobile device 20 to perform functions described above and others related to communication control, audio signal processing, control for the audio signal processing, still and moving image processing and control, and other kinds of signal processing. The controller 110 may perform these functions by executing instructions stored in a memory 150. Alternatively, or in addition to the local storage of the memory 150, the functions may be executed using instructions stored on an external device accessed on a network or on a non-transitory computer readable medium. As relevant above to notification generation, the controller 110 may execute instructions allowing the controller 110 to function as the display control unit 211.

In an embodiment, the mobile device 20 may include a BIM system section 111 having, at least, a controller that is separate from the controller 110. The BIM system section 111 controller can include one or more CPUs and may be configured to control application of electrical stimuli, measurement of electrical stimuli, and analysis of electrical stimuli applied to a head of a patient. Measurement, or acquisition, of the electrical stimuli may be aided by a data acquisition system of the BIM system section 111. The BIM system section 111 controller may be further configured to act as a voltage-controlled current source in the event the electrical stimulus is applied as a current injection. Of course, the BIM system section 111 need not have a separate controller. In this instance, control of the BIM system section 111 may be provided by the controller 110.

The memory 150 can be a storage unit and can include, but not be limited to, Read Only Memory (ROM), Random Access Memory (RAM), or a memory array including a combination of volatile and non-volatile memory units. The memory 150 may be utilized as working memory by the controller 110 while executing the processes and algorithms of the present disclosure. Additionally, the memory 150 may be used for long-term storage, e.g., of image data and information related thereto.

The mobile device 20 includes a control line CL and data line DL as internal communication bus lines. Control data to/from the controller 110 may be transmitted through the control line CL. The data line DL may be used for transmission of voice data, display data, etc.

The antenna 101 transmits/receives electromagnetic wave signals between base stations for performing radio-based communication, such as the various forms of cellular telephone communication. The wireless communication processor 102 controls the communication performed between the mobile device 20 and other external devices via the antenna 101. For example, the wireless communication processor 102 may control communication between base stations for cellular phone communication.

In an embodiment, the wireless communication processor 102 controls communication performed by the mobile device 20 to query a database that includes reference values of impedance metrics corresponding to a representative population of patients or to specific patient cohorts that can be matched to a current patient, in real-time. In this way, accurate baseline values upon which a determination of ischemia or hemorrhage (or other pathology) can be determined, are obtained.

The speaker 104 emits an audio signal corresponding to audio data supplied from the voice processor 103. The microphone 105 detects surrounding audio and converts the detected audio into an audio signal. The audio signal may then be output to the voice processor 103 for further processing. The voice processor 103 demodulates and/or decodes the audio data read from the memory 150 or audio data received by the wireless communication processor 102 and/or a short-distance wireless communication processor 107. Additionally, the voice processor 103 may decode audio signals obtained by the microphone 105. In an embodiment, the notification generation described above can be provided via the speaker 104.

The exemplary mobile device 20 may also include a display 120, a touch panel 130, an operation key 140, and a short-distance communication processor 107 connected to an antenna 106. The display 120 may be a Liquid Crystal Display (LCD), an organic electroluminescence display panel, or another display screen technology. In addition to displaying still and moving image data, the display 120 may display operational inputs, such as numbers or icons which may be used for control of the mobile device 20. The display 120 may additionally display a GUI for a user to control aspects of the mobile device 20 and/or other devices. Further, the display 120 may display characters and images received by the mobile device 20 and/or stored in the memory 150 or accessed from an external device on a network. For example, the mobile device 20 may access a network such as the Internet and display text and/or images transmitted from a Web server. In an embodiment, the notification generation described above can be provided via the display 120 or the touch panel 130.

The touch panel 130 may include a physical touch panel display screen and a touch panel driver. The touch panel 130 may include one or more touch sensors for detecting an input operation on an operation surface of the touch panel display screen. The touch panel 130 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 130 may detect when the stylus approaches/contacts the operation surface of the touch panel display (similar to the case in which a finger is used for the touch operation).

In certain aspects of the present disclosure, the touch panel 130 may be disposed adjacent to the display 120 (e.g., laminated) or may be formed integrally with the display 120. For simplicity, the present disclosure assumes the touch panel 130 is formed integrally with the display 120 and therefore, examples discussed herein may describe touch operations being performed on the surface of the display 120 rather than the touch panel 130. However, the skilled artisan will appreciate that this is not limiting.

For simplicity, the present disclosure assumes the touch panel 130 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 130 may include transparent electrode touch sensors arranged in the X-Y direction on the surface of transparent sensor glass.

The touch panel driver may be included in the touch panel 130 for control processing related to the touch panel 130, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 130 may detect a position of a user's finger around an edge of the display panel 120 (e.g., gripping a protective case that surrounds the display/touch panel). Signals may be transmitted by the touch panel driver, e.g. in response to a detection of a touch operation, in response to a query from another element based on timed data exchange, etc.

The touch panel 130 and the display 120 may be surrounded by a protective casing, which may also enclose the other elements included in the mobile device 20. In certain embodiments, a position of the user's fingers on the protective casing (but not directly on the surface of the display 120) may be detected by the touch panel 130 sensors. Accordingly, the controller 110 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 110 may be configured to detect which hand is holding the mobile device 20, based on the detected finger position. For example, the touch panel 130 sensors may detect a plurality of fingers on the left side of the mobile device 20 (e.g., on an edge of the display 120 or on the protective casing), and detect a single finger on the right side of the mobile device 20. In this exemplary scenario, the controller 110 may determine that the user is holding the mobile device 20 with his/her right hand because the detected grip pattern corresponds to an expected pattern when the mobile device 20 is held only with the right hand.

The operation key 140 may include one or more buttons or similar external control elements, which may generate an operation signal based on a detected input by the user. In addition to outputs from the touch panel 130, these operation signals may be supplied to the controller 110 for performing related processing and control. In certain aspects of the present disclosure, the processing and/or functions associated with external buttons and the like may be performed by the controller 110 in response to an input operation on the touch panel 130 display screen rather than the external button, key, etc. In this way, external buttons on the mobile device 20 may be eliminated in lieu of performing inputs via touch operations, thereby improving water-tightness.

The antenna 106 may transmit/receive electromagnetic wave signals to/from other external apparatuses, and the short-distance wireless communication processor 107 may control the wireless communication performed between the other external apparatuses. Bluetooth, IEEE 802.11, and near-field communication (NFC) are non-limiting examples of wireless communication protocols that may be used for inter-device communication via the short-distance wireless communication processor 107.

The mobile device 20 may include a motion sensor 108. The motion sensor 108 may detect features of motion (i.e., one or more movements) of the mobile device 20. For example, the motion sensor 108 may include an accelerometer to detect acceleration, a gyroscope to detect angular velocity, a geomagnetic sensor to detect direction, a geo-location sensor to detect location, etc., or a combination thereof to detect motion of the mobile device 20. In certain embodiments, the motion sensor 108 may generate a detection signal that includes data representing the detected motion. For example, the motion sensor 108 may determine a number of distinct movements in a motion (e.g., from start of the series of movements to the stop, within a predetermined time interval, etc.), a number of physical shocks on the mobile device 20 (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller 110, whereby further processing may be performed based on data included in the detection signal. The motion sensor 108 can work in conjunction with a Global Positioning System (GPS) section 160. The GPS section 160 detects the present position of the terminal device 100. The information of the present position detected by the GPS section 160 is transmitted to the controller 110. An antenna 161 is connected to the GPS section 160 for receiving and transmitting signals to and from a GPS satellite.

The mobile device 20 may include a camera section 109, which includes a lens and shutter for capturing photographs of the surroundings around the mobile device 20. In an embodiment, the camera section 109 captures surroundings of an opposite side of the mobile device 20 from the user. The images of the captured photographs can be displayed on the display panel 120. A memory section saves the captured photographs. The memory section may reside within the camera section 109 or it may be part of the memory 150. The camera section 109 can be a separate feature attached to the mobile device 20 or it can be a built-in camera feature.

Figure 11:
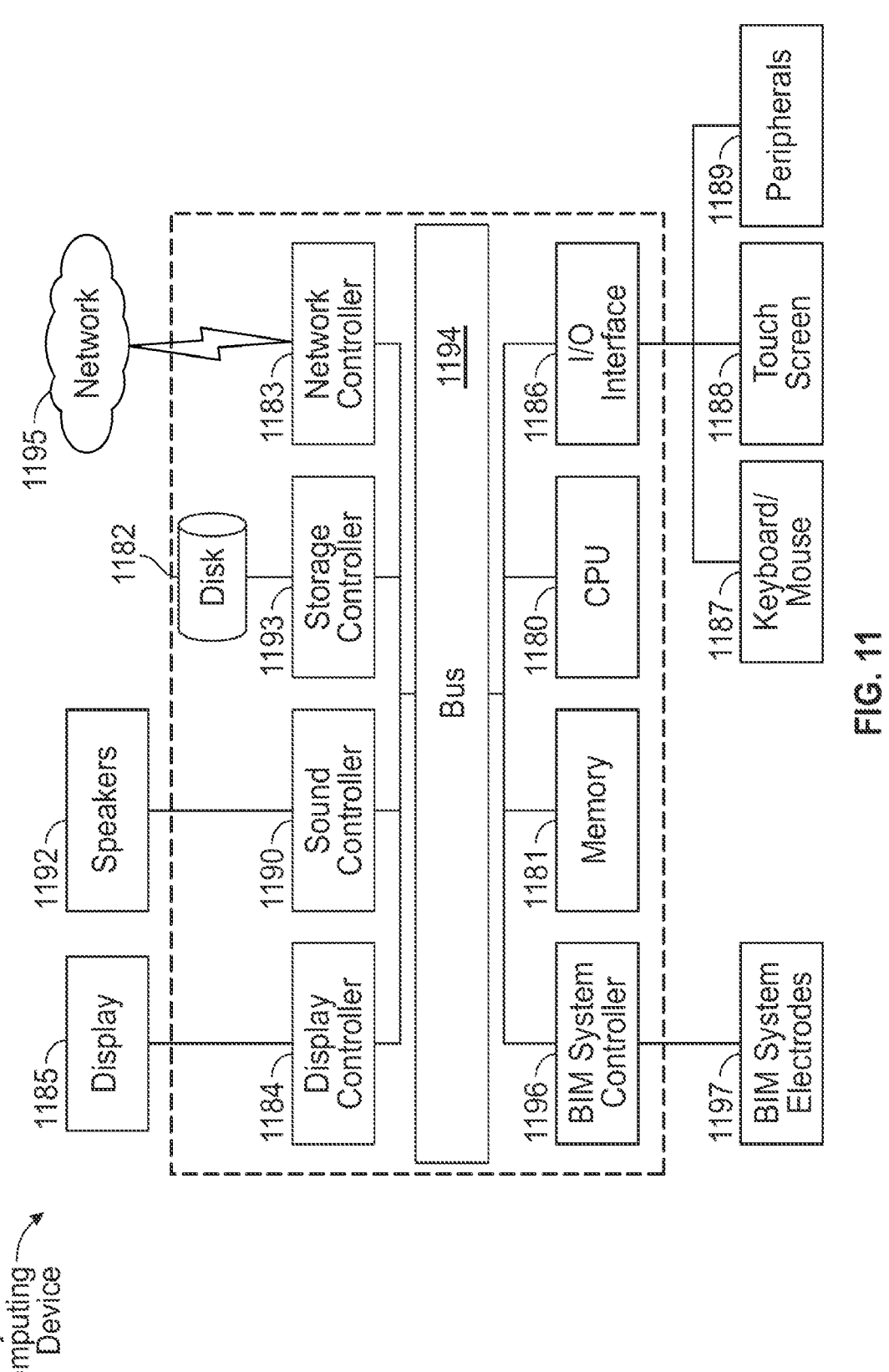
FIG. 11 is a hardware diagram of a computing device that can be used in conjunction with a bioimpedance monitoring system, according to an exemplary embodiment of the present disclosure.

In view of the regional implementations of the BIM system described above, a hardware description of a BIM system computing device, according to exemplary embodiments, is described with reference to FIG. 11. In FIG. 11, the BIM system computing device includes a CPU 1180 which performs the processes described above/below. The process data and instructions may be stored in memory 1181. These processes and instructions may also be stored on a storage medium disk 1182 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the BIM system computing device communicates, such as a server or computer.

Further, the claimed advancements may be provided as a utility application, background daemon, or component of an operating system, or combination thereof, executing in conjunction with CPU 1180 and an operating system such as Microsoft Windows 7, UNIX, Solaris, LINUX, Apple MAC-OS and other systems known to those skilled in the art.

The hardware elements in order to achieve the BIM system computing device may be realized by various circuitry elements, known to those skilled in the art. For example, CPU 1180 may be a Xenon or Core processor from Intel of America or an Opteron processor from AMD of America, or may be other processor types that would be recognized by one of ordinary skill in the art. Alternatively, the CPU 1180 may be implemented on an FPGA, ASIC, PLD or using discrete logic circuits, as one of ordinary skill in the art would recognize. Further, CPU 1180 may be implemented as multiple processors cooperatively working in parallel to perform the instructions of the inventive processes described above.

The BIM system computing device in FIG. 11 also includes a network controller 1183, such as an Intel Ethernet PRO network interface card from Intel Corporation of America, for interfacing with network 1195. As can be appreciated, the network 1195 can be a public network, such as the Internet, or a private network such as an LAN or WAN network, or any combination thereof and can also include PSTN or ISDN sub-networks. The network 1195 can also be wired, such as an Ethernet network, or can be wireless such as a cellular network including EDGE, 3G and 4G wireless cellular systems. The wireless network can also be WiFi, Bluetooth, or any other wireless form of communication that is known.

The BIM system computing device further includes a display controller 1184, such as a NVIDIA GeForce GTX or Quadro graphics adaptor from NVIDIA Corporation of America for interfacing with display 1185, such as a Hewlett Packard HPL2445w LCD monitor, and displaying a notification regarding a health condition of a patient. A general purpose I/O interface 1186 interfaces with a keyboard and/or mouse 1187 as well as a touch screen panel 1188 on or separate from display 1185. The general purpose I/O interface 1186 may also interface with peripherals 1189, such as a database of reference values of impedance metrics. The database may include reference values of impedance metrics corresponding to a representative population of patients or to specific patient cohorts that can be matched to a current patient, in real-time, to provide accurate baseline values upon which a determination of ischemia or hemorrhage (or other pathology) can be determined.

A sound controller 1190 is also provided in the BIM system computing device, such as Sound Blaster X-Fi Titanium from Creative, to interface with speakers/microphone 1192 thereby providing sounds and/or music, or notifications regarding a health condition of a patient.

The general purpose storage controller 1193 connects the storage medium disk 1182 with communication bus 1194, which may be an ISA, EISA, VESA, PCI, or similar, for interconnecting all of the components of the BIM system computing device. A description of the general features and functionality of the display 1185, keyboard and/or mouse 1187, as well as the display controller 1184, storage controller 1193, network controller 1183, sound controller 1190, and general purpose I/O interface 1186 is omitted herein for brevity as these features are known.

In an embodiment, the BIM system computing device of FIG. 11 includes a BIM system controller 1196 for interacting with and controller electrodes of the BIM system that are arranged on a head of a patient. The BIM system controller 1196 may be integrated with, or independent from, CPU 1180, and may be configured to apply, measure, and analyze electrical stimuli provided to the head of the patient.

Figure 12:
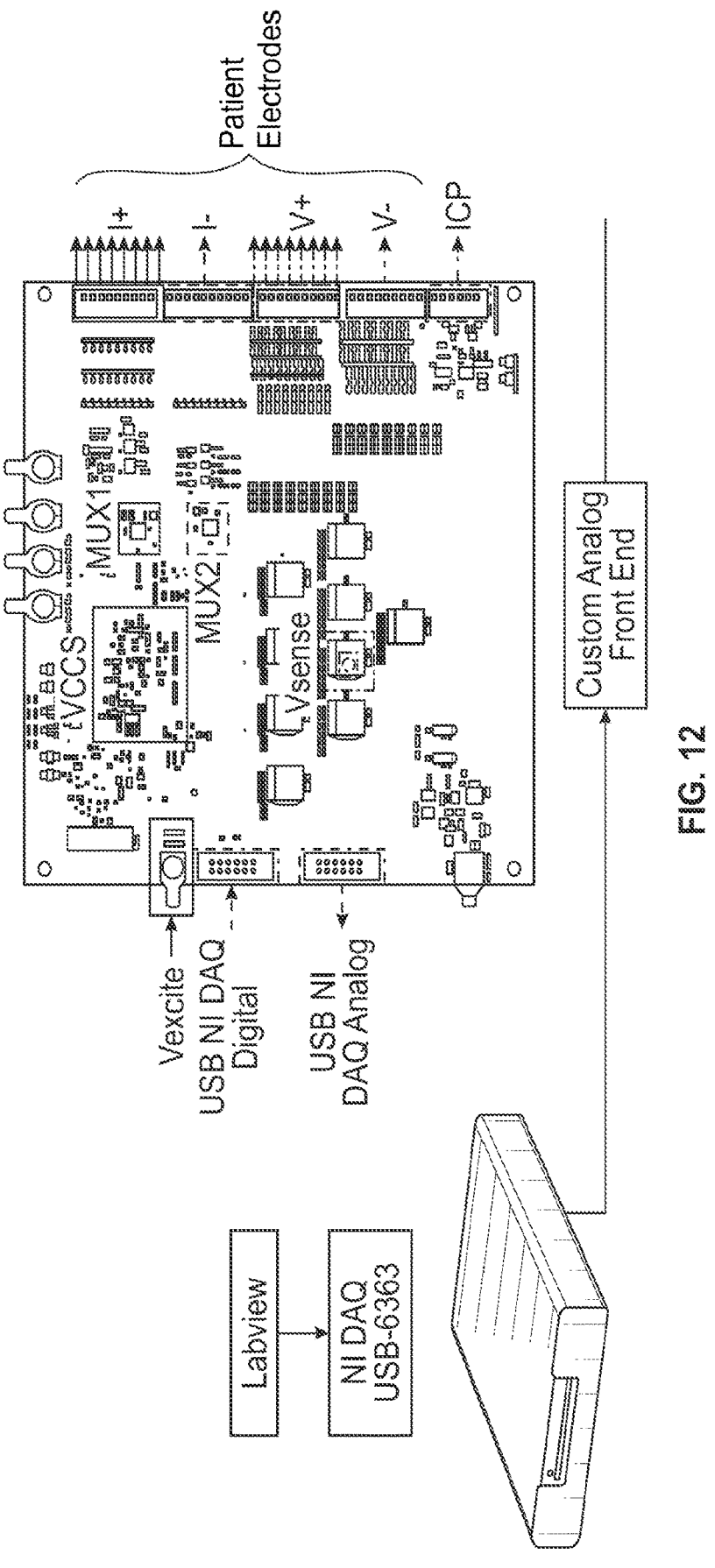
FIG. 12 is an illustration of hardware components of a bioimpedance monitoring system, according to an exemplary embodiment of the present disclosure.

According to an exemplary embodiment, and as shown in FIG. 12, the BIM system may include a computing device having controlling access to a data acquisition module and a custom analog front end printed circuit board (FEPCB) for interfacing with electrodes of the BIM system. The data acquisition module may be, in a non-limiting example, a USB-6363 controlled by LabView programming (National Instruments, Austin, TX). The FEPCB may utilize 16 surface electrode channels. Ag/AgCl scalp electrodes (EK310 Electrodes, Kendall Care, NY) were selected to minimize CT artifacts.

A Howland voltage controlled current source (VCCS) provided precision current control over the range of 0.5-5.0 mA. Current and voltage were sampled from each channel at 50 kHz and the amplitudes extracted using a matched filter[60]; impedances were computed as the ratio of voltage to current at a rate of 50 Hz with averaging of 1000 samples per data point. The VCCS injects a 2.3 $mA_{pp}$ sinusoidal current at 50 kHz and the BIM system captures complex impedance data by computing the ratio of the induced potential difference and this injected current.

Precision of the system was characterized through voltage measurement of four discrete resistive loads representative of expected in vivo ranges (100Ω, 500Ω, 1 kΩ and 2 kΩ) with excitation current of 50 kHz and 2.3 $mA_{PP}$. Average precision was 84.3+/−2.0 dB across loads. Measured voltage was linear with load and test loads of 800Ω and 1500Ω showed measurement accuracy of 99.1% and 99.8%, respectively. The device bandwidth extends to 100 kHz, though it is typically operated at 50 kHz.

The BIM instrumentation is designed to collect data at 50 samples per second, exceeding the 30 sps requirement (Table 1). The custom FEAFE provided multiplexing between channels and successfully captured broadband (10 Hz-100 kHz) impedances with sufficient accuracy (99.7%), precision (SNR=84.23 dB), and temporal stability (<0.03% CV) for a TBI monitoring application.

Non-Limiting Experimental Data

The potential spatial mapping capabilities of the BIM system were investigated. An eight-sector map linked to the eight system channels provides a mechanism to spatially localize intracranial changes. A cylindrical acrylic tank filled with saline (σ=0.1 S/m) and instrumented with circumferential tab electrodes and a centrally located DBS electrode simulated the intracranial imaging scenario.

As an initial proof of concept, a linear stage was connected to a custom script and enabled precise volume control of a fogarty balloon. The balloon was placed in the tank in a specific sector and inflated from 0 to 3 mL at 200 uL/min.

Impedance data were collected continuously throughout the inflation and plotted on color maps at minute time points. Each sector of the color map represents raw impedance values differenced from their baseline (no inflation) value.

Figure 13:
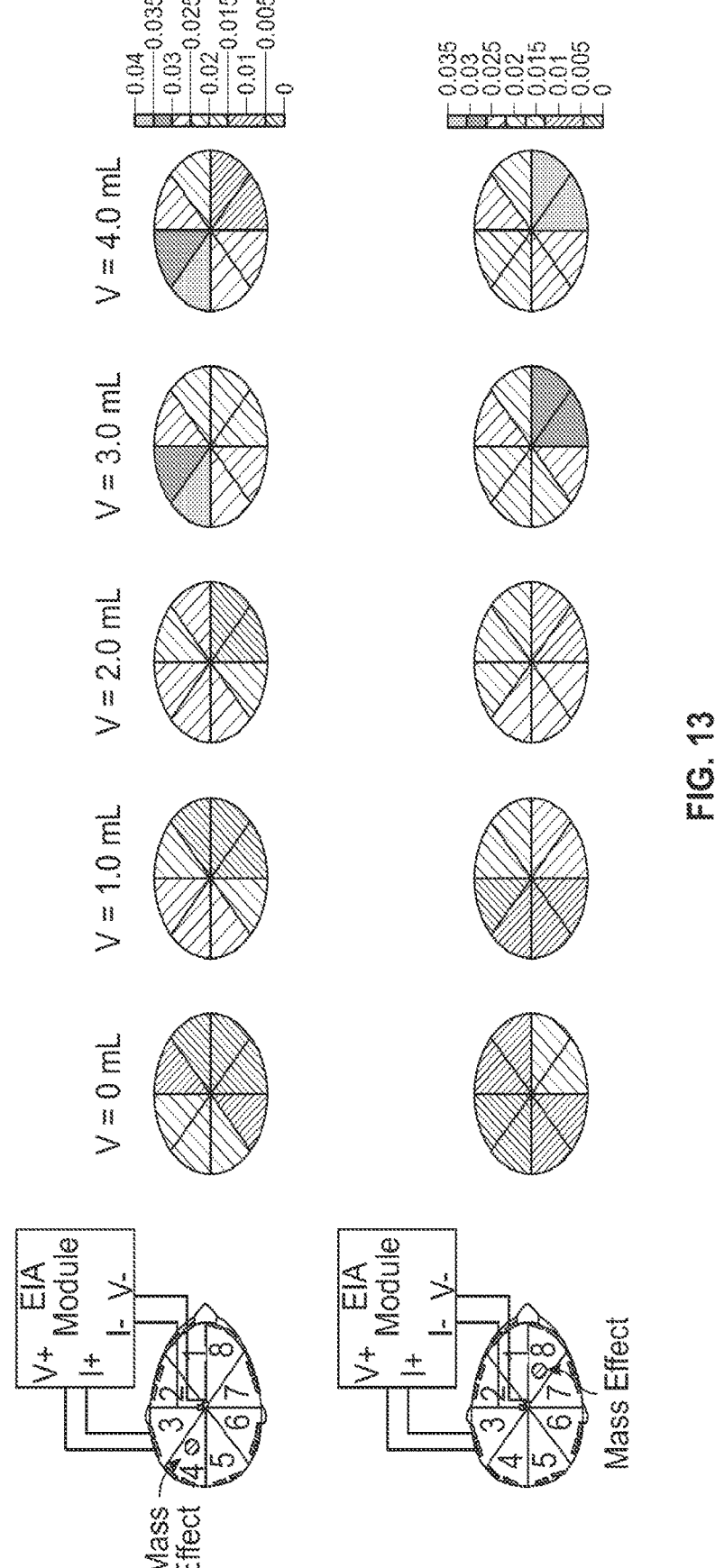
FIG. 13 is a color map displaying raw impedance values across regions of a phantom, according to an exemplary embodiment of the present disclosure.

On a different day, a similar protocol was performed and the inclusion moved to verify tracking. The balloon was inflated from 0 to 4 mL by a Chemyx OEM linear stage. Color maps were analyzed for each experiment by computing the impedance (Z) change that occurred in each sector over time with respect to the baseline measurement collected from the saline tank prior to inflation, as shown in FIG. 13. The initial volume collection was at 0 mL, but following a baseline average. For this reason there may be small differences between baseline and V=0 mL, as can be seen in the slight dark blue striations at that initial step. For the following steps, an obvious impedance change associated with a controlled inclusion volume change was observed and tracked with mass effect location. Impedance increased in all sectors as a function of the increased mass effect size. Additionally, the sectors with the maximum impedance changes were associated with the location of the mass effect.

Localized detection was evident in as little as 1 mL injection, with sectors 4 and 8 showing larger impedances than the other sectors at this volume change. This localized elevated impedance was evident at each volume increment up to 4 mL. While the maximum impedance change was correctly associated with the location of the inclusion there was moderate variability amongst the other sectors; however, the sectors adjacent to the mass effect location generally had the next highest impedance values, suggesting that the local sensitivity is broader then a single sector.

Lastly, metal and plastic inclusions (in the form of 5 mm diameter cylindrical rods) placed throughout the tank provided a mechanism to image focal impedance changes between two event types (high Z and low Z). The BIM correctly identified and mapped both inclusion types to their relative sector. The successful spatial tracking observed supports our hypothesis that impedance may be used for focal injury detection.

Evaluation of Non-Invasive Intracranial Interrogation in Pigs

Methods

Bioimpedance Instrumentation

The current AFE setup has the capability to MUX between eight channels of four electrodes (I+V+I–V–). Traditionally these have been ordered such that eight scalp electrode pairs (I+V+) collect sequentially with the indwelling electrode held constant as a sink (I–V–). For the non-invasive validation we were limited to the same hardware. While eight scalp channels would be ideal, we instrumented the animals with six scalp electrode pairs, a right orbit pair, a left orbit pair and a soft palate pair. The scalp electrodes will be arranged to cover the superior and lateral aspect of the cranium with a symmetrical distribution between frontal, temporal occipital and parietal lobes. Both the right and left orbits were setup as potential sources and sinks to explore the ability to interrogate the frontal cortex immediately behind the eyes should you source from one eye and sink to the other, or source from each and sink to the soft palate. This also has the potential to allow comparison of asymmetries of sides. Ag/AgCl tab electrodes were used on top of eyelids and long needle electrodes, commonly used in neural monitoring for patients, were secured in soft palate of the pig.

Ischemic Model

The animal underwent focal cerebral ischemia (FCI) using a previously validated animal model for FCI. We created a focal change in perfusion using a middle cerebral artery occlusion (MCAO) model developed for minipigs. Briefly, following intubation and electrode placement, a frontotemporal approach with orbital rim osteotomy is used to access the MCA. A bone flap is removed from just above the eye (and preserved for later replacement to maintain proper current pathways), the dura opened and gentle retraction used to visualize the MCA. Once located, the MCA is electrocoagulated over a 1.5 mm distance and transected to ensure complete occlusion. Retraction is removed, the bone replaced and suture is used to close the incision. This approach creates a local region of ischemia. We expect to see different sectors of decreased perfusion (increased ischemia/impedance) for the FCI maneuvers.

Data Collection

To enable confident interpretation of the data, baseline was defined as post-craniotomy and pre-ischemic infarct. In this sense any asymmetries due to the surgery itself would be consistent between baseline and stroke, helping to isolate observed impedance changes to the induced lesion, not the process of surgical access. The bone flap was replaced and skin sutured closed in the same method for both collections. Periodic CT scans of the cranium were obtained throughout the experiment and served as the reference for identifying intracranial changes during the peri-stroke period. Baseline $pCO_2$ (blood gas), ECG, and ABP signatures also were recorded in synchrony with impedance data. The pig remained in this configuration for 30 minutes to ensure stability. This initial period will eventually be used to validate repeatability of data acquisition during the stabilization period prior to instigating vascular occlusion or hemorrhage to simulate stroke. Impedance was sampled at 50 Hz with an applied 2.3 mA current at 50 kHz frequency.

Initial Results: Stroke Animal Model

Of the three stroke cases, the first two were critical to master what was a fairly extensive ischemic model. Gaining surgical access, understanding the porcine anatomy, obtaining the correct micro-tools and operating under a scope all were aspects learned and mastered during the first two cases.

Impedance data was collected on the second case, however baseline was collected pre-surgery and the differences observed unable to confidently be defined as due to stroke or due to the surgery itself. This protocol was changed to match that listed above for the third pig. During surgery our neurosurgical collaborators (Dr. David Bauer and Dr. Daniel Calnan) successfully accessed the MCA and induced ischemia. CT angiograms visualized the cerebral vasculature pre- and post-ischemia and showed asymmetric loss of perfusion.

Initial Results: Impedance

Impedance signals for the third pig were compared between channels sensing the ischemic stroke region and those sensing the remaining healthy brain. Channels were grouped by location correlating to the ischemic region, with midline channels being grouped as 'healthy'. Each channel for the stroke period was then divided by its own pre-stroke post-craniotomy baseline. Scalp electrode patterns were then grouped by their sink so that invasive and non-invasive approaches could be compared.

Figure 14:
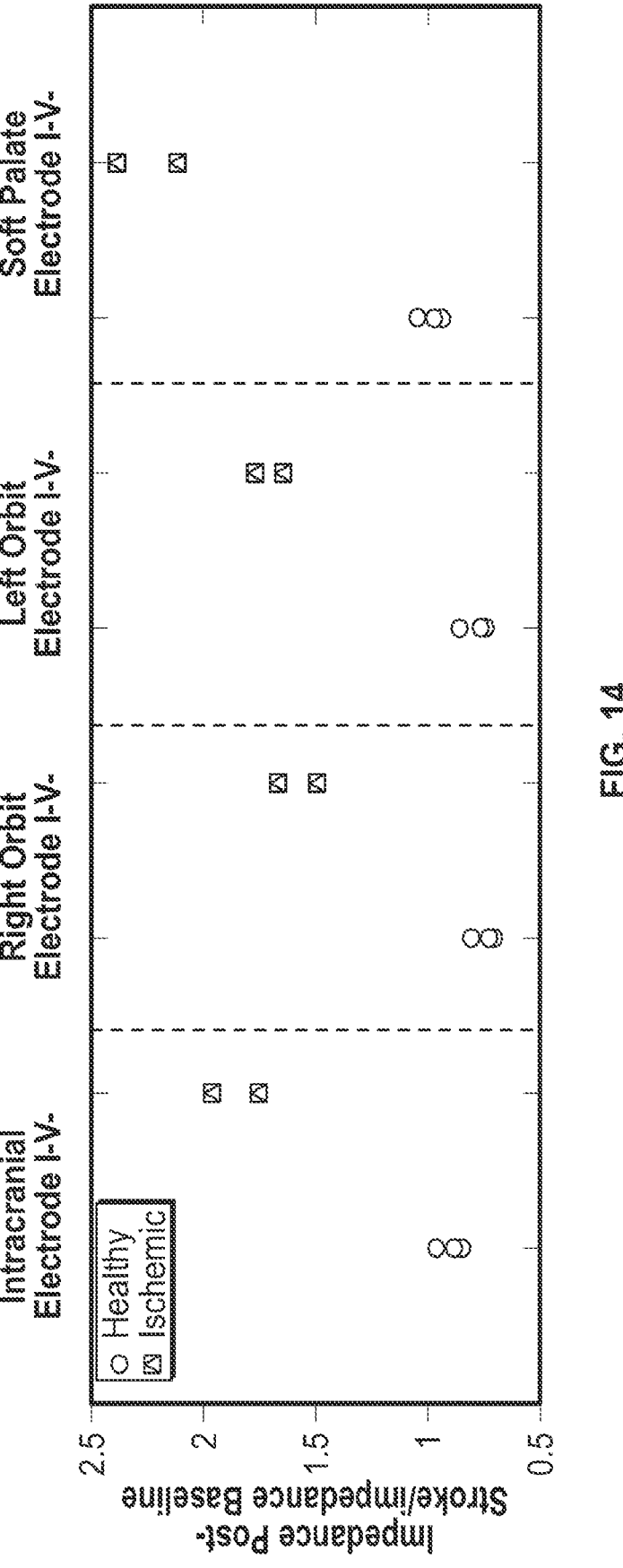
FIG. 14 is a graphical illustration of a comparison of impedance values between healthy animals and ischemic animals when different conductive locations are used, according to an exemplary embodiment of the present disclosure.

FIG. 14 shows a clear separation between healthy and ischemic impedance. Additionally, when split between I-V-sink locations, we see equivalent contrast between our ischemic and healthy tissue independent of an invasive (intracranial) or non-invasive approach (orbit and soft palate). While only one case, this provides exciting initial data and supports our hypothesis for non-invasive detection of ischemic stroke and progressing with the proposed non-invasive stroke cohort.

Hardware Development and Prototype Design

Hardware

Figure 15:
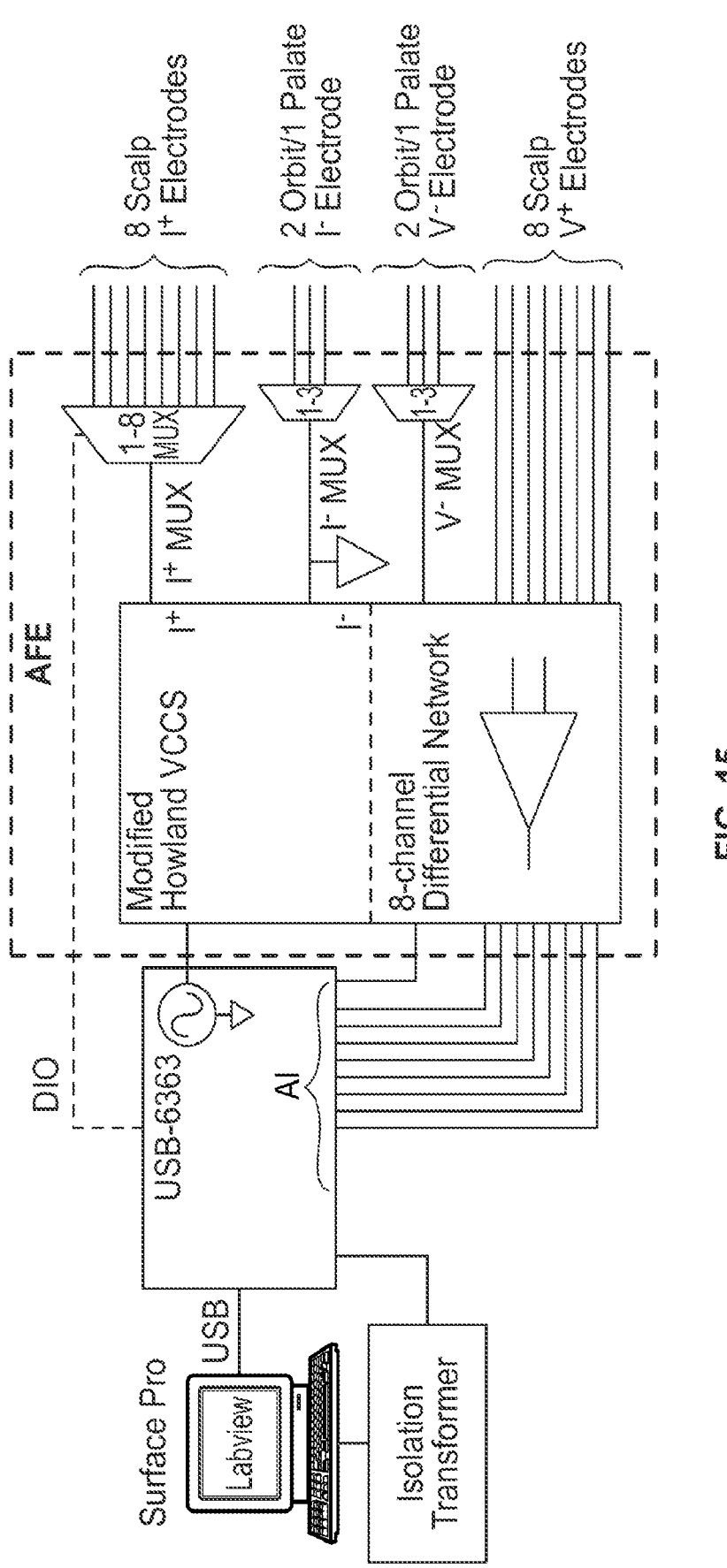
FIG. 15 is a schematic of a hardware component of a bioimpedance monitoring system, according to an exemplary embodiment of the present disclosure.

The BIM system enables intracranial sensing through anatomic windows into the intracranial space (i.e. orbits and palate electrodes). An NI USB 6259 data acquisition unit (National Instruments, Austin, TX) is used as a signal generation and voltage-sensing module. The analog front end (AFE) can include a series of 1-to-3 multiplexors to enable switching between multiple return electrode sites (I⁻ & V⁻). Specifically, the BIM system includes a small form-factor printed circuit board (PCB) that will incorporate a modified Howland current source and a multiplexing network to enable impedance measurements from multiple electrode combinations, as shown in FIG. 15. The BIM system is designed to record tetrapolar impedances over the frequency range of 1 kHz to 1 MHz. The impedance sensing circuits can be interfaced to a set of 8 scalp electrodes and to two orbital and one soft palate electrodes through use of on-board multiplexors (ADG1608, Analog Devices). Multiplexors can switch between different sets of electrodes. All voltage and current signals can be sensed through the NI DAQ and processed in LabView. The front-end PCB can be designed in Eagle Layout and fabricated by a PCB manufacturer we have previously used (e.g. Advanced Assembly, Aurora, CO). This hardware enables both a TBI configuration (eight circumferential surface channels and a fixed indwelling sink channel) or a stroke configuration (eight circumferential surface channels, two paired orbital electrodes and a soft palate electrode).

Software

Software for the fully integrated system controls the impedance acquisition module, analyzes impedance signals, and displays the data. Custom software is written in LabView to communicate with the impedance acquisition system. The software is programmed to set a specific signal frequency (or range of frequencies), set a specific frame rate, set a pattern file which switches between the different sink/source electrode pairs, and receive data transmitted from the DAQ module. A custom script is written capable of selecting which MUX drive algorithm is needed (the nine channel or the twelve channel).

Surface Electrodes

Novel non-invasive electrode design is required to create a prototype capable of being worn clinically on an ICU patient, for stroke monitoring and not disturb the current monitoring setting. A 3D printed flexible headband is designed with slots of single-use tab electrodes (Kendall EK310) for the cranial surface channels. For the TBI cohort, a coupled DBS (or similar alternative) stylet is designed which allows quick interface to the ICP monitor during clinical placement. For non-invasive stroke monitoring, a tongue depressor type electrode is designed with similar style orbit electrodes.

Impact

The BIM System has the potential to reduce patient time-to-treatment, improve patient outcomes, and provide a valuable tool with safe continual monitoring for clinician use. The concept of intracranial interrogation discussed here has the potential to impact approaches to electrode-based cranial monitoring.

The innovative impacts of bioimpedance-based cerebral monitoring would expand beyond TBI and stroke and enable future novel technology developments. For example, hydrocephalus monitoring, recurring brain bleeds, tumor resection monitoring and more all rely upon intracranial pressure only. If BIM is validated as a potential technology for intracranial trauma monitoring, the impacts of this novel application of a standard technology could extend far beyond what has been presented here today.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A system for non-invasive intracranial monitoring, comprising two or more affecting electrodes arranged between a conductive location of a cranium of a patient and a location on a scalp of the patient, two or more effected electrodes arranged between the conductive location of the cranium of the patient and the location on the scalp of the patient, and processing circuitry configured to apply an electrical stimulus between the two or more affecting electrodes, measure an electrical stimulus differential between the two or more effected electrodes, calculate, for the two or more effected electrodes, a value of an impedance metric, and identify, based on the calculated value of the impedance metric, a health condition of the patient.

(2) The system of (1), wherein the processing circuitry is further configured to identify the health condition of the patient by determining, based on the calculated value of the impedance metric, a differential impedance value relative to a reference impedance value selected from a library of reference impedance values, the reference value being selected based on biometrics of the patient, and identifying, based on the determined differential impedance value, the health condition of the patient.

(3) The system of either (1) or (2), wherein the two or more effected electrodes include a plurality of effected electrodes arranged symmetrically around the scalp of the patient, the two or more affecting electrodes include a plurality of affecting electrodes arranged around the scalp of the patient, one of the plurality of affecting electrodes being proximate one of the plurality of symmetrically-arranged effected electrodes, each one of the plurality of affecting electrodes and a respective one of the plurality of symmetrically-arranged effected electrodes defining a regional pair, and the processing circuitry is further configured to apply a regional electrical stimulus between an affecting electrode arranged at the conductive location and one of the plurality of affecting electrodes arranged around the scalp of the patient and proximate one of the plurality of symmetrically-arranged effected electrodes, the one of the plurality of affecting electrodes and the proximate one of the plurality of symmetrically-arranged effected electrodes defining a first regional pair of electrodes corresponding to a first region of a brain of the patient, measure an electrical stimulus differential between an effected electrode arranged at the conductive location and the proximate one of the plurality of symmetrically-arranged effected electrodes of the first regional pair of electrodes, calculate, for the first region of the brain of the patient and based on the measured electrical stimulus differential, a value of a first regional impedance metric, and identify, based on the calculated value of the first regional impedance metric, a focal health condition of the patient.

(4) The system of any one of (1) to (3), wherein the processing circuitry is further configured to identify the focal health condition of the patient by comparing the calculated value of the first regional impedance metric to a reference value selected from a library of reference values, the reference value being selected based on biometrics of the patient, and identifying the focal health condition of the patient based on the comparison.

(5) The system of any one of (1) to (4), wherein the processing circuitry is further configured to apply a subsequent regional electrical stimulus between an affecting electrode arranged at the conductive location and an affecting electrode, of a second regional pair of electrodes, arranged around the scalp of the patient, the second regional pair of electrodes corresponding to a second region of the patient, measure a subsequent electrical stimulus differential between an effected electrode arranged at the conductive location and an effected electrode of the second regional pair of electrodes, calculate, for the second region of the brain of the patient and based on the measured subsequent electrical stimulus differential, a value of a second regional impedance metric, compare the calculated value of the first regional impedance metric and the calculated value of the second regional impedance metric, and identify, based on the comparison, a differential focal health condition of the patient.

(6) The system of any one of (1) to (5), wherein the processing circuitry is further configured to identify the differential focal health condition of the patient by performing a ratiometric analysis as the comparison of the calculated value of the first regional impedance metric and the calculated value of the second regional impedance metric.

(7) The system of any one of (1) to (6), wherein the processing circuitry is further configured to calculate a time-averaged value of the impedance metric as the calculated value.

(8) The system of any one of (1) to (7), wherein the processing circuitry is further configured to calculate a rate of change of values of the impedance metric, over a predefined period of time, as the calculated value.

(9) The system of any one of (1) to (8), wherein the processing circuitry is further configured to apply an electrical current as the electrical stimulus between the two or more affecting electrodes, and measure a voltage potential as the electrical stimulus differential between the two or more effected electrodes.

(10) The system of any one of (1) to (9), wherein the processing circuitry is further configured to apply the electrical current at a value between 0.1 milliamperes and 10.0 milliamperes.

(11) The system of any one of (1) to (10), wherein the processing circuitry is further configured to apply the electrical current at multiple frequencies.

(12) The system of any one of (1) to (11), wherein the circuitry is further configured to apply a voltage potential as the electrical stimulus between the two or more affecting electrodes, and measure an electrical current as the electrical stimulus differential between the two or more effected electrodes.

(13) The system of any one of (1) to (12), wherein the processing circuitry is further configured to apply the voltage potential at a value between 0.5 Volts and 3 Volts.

(14) The system of any one of (1) to (13), wherein the processing circuitry is further configured to identify the health condition of the patient as one of ischemic, hemorrhagic, or edemic.

(15) A method for non-invasive intracranial monitoring, comprising applying, by processing circuitry, an electrical stimulus between two or more affecting electrodes, the two or more affecting electrodes being arranged between a conductive location of a cranium of a patient and a location on a scalp of the patient, measuring, by the processing circuitry, an electrical stimulus differential between two or more effected electrodes, the two or more effected electrodes being arranged between the conductive location of the cranium of the patient and the location on the scalp of the patient, calculating, by the processing circuitry and for the two or more effected electrodes, a value of an impedance metric, and identifying, by processing circuitry and based on the calculated value of the impedance metric, a health condition of the patient.

(16) The method of (15), wherein the applying the electrical stimulus between the two or more affecting electrodes includes applying the electrical stimulus via, as the conductive location of the cranium of the patient, one or more locations selected from a group including a right orbit, a left orbit, a soft palate, and a base of a neck of the patient.

(17) A system for non-invasive intracranial monitoring, comprising electrodes arranged between a conductive location of a cranium of a patient and a location on a scalp of the patient, and processing circuitry configured to apply an electrical stimulus between the electrodes, measure an electrical stimulus differential between the electrodes, calculate, for the electrodes, a value of an impedance metric, and identify, based on the calculated value of the impedance metric, a health condition of the patient.

(18) The system of (17), wherein the processing circuitry is further configured to identify the health condition of the patient by determining, based on the calculated value of the impedance metric, a differential impedance value relative to a reference impedance value selected from a library of reference impedance values, the reference value being selected based on biometrics of the patient, and identifying, based on the determined differential impedance value, the health condition of the patient.

(19) The system of either of (17) or (18), wherein the electrodes include a plurality of electrodes arranged symmetrically around the scalp of the patient, each of the plurality of symmetrically-arranged electrodes around the scalp of the patient define a region of the brain, and the processing circuitry is further configured to apply a regional electrical stimulus between an electrode arranged at the conductive location and a first one of the plurality of symmetrically-arranged electrodes, the regional electrical stimulus being applied to a corresponding first region of the brain, measure an electrical stimulus differential between the electrode arranged at the conductive location and the first one of the plurality of symmetrically-arranged electrodes of the first region of the brain, calculate, for the first region of the brain of the patient and based on the measured electrical stimulus differential, a value of a first regional impedance metric, and identify, based on the calculated value of the first regional impedance metric, a focal health condition of the patient.

(20) The system of any one of (17) to (19), wherein the processing circuitry is further configured to identify the focal health condition of the patient by comparing the calculated value of the first regional impedance metric to a reference value selected from a library of reference values, the reference value being selected based on biometrics of the patient, and identifying the focal health condition of the patient based on the comparison.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system for non-invasive intracranial monitoring, comprising:

two or more affecting electrodes arranged between a conductive location of a cranium of a patient and a location on a scalp of the patient;

two or more effected electrodes arranged between the conductive location of the cranium of the patient and the location on the scalp of the patient; and processing circuitry configured to apply a voltage potential as an electrical stimulus between the two or more affecting electrodes, measure an electric current as an electrical stimulus differential between the two or more effected electrodes, calculate, for the two or more effected electrodes, a value of an impedance metric, and identify, based on the calculated value of the impedance metric, a health condition of the patient, wherein the two or more effected electrodes include a plurality of effected electrodes arranged symmetrically around the scalp of the patient, the two or more affecting electrodes include a plurality of affecting electrodes arranged around the scalp of the patient, one of the plurality of affecting electrodes being proximate one of the plurality of symmetrically-arranged effected electrodes, each one of the plurality of affecting electrodes and a respective one of the plurality of symmetrically-arranged effected electrodes defining a regional pair, and the processing circuitry is further configured to apply a regional electrical stimulus between an affecting electrode arranged at the conductive location and one of the plurality of affecting electrodes arranged around the scalp of the patient and proximate one of the plurality of symmetrically-arranged effected electrodes, the one of the plurality of affecting electrodes and the proximate one of the plurality of symmetrically-arranged effected electrodes defining a first regional pair of electrodes corresponding to a first region of a brain of the patient, measure an electrical stimulus differential between an effected electrode arranged at the conductive location and the proximate one of the plurality of symmetrically-arranged effected electrodes of the first regional pair of electrodes, calculate, for the first region of the brain of the patient and based on the measured electrical stimulus differential, a value of a first regional impedance metric, identify, based on the calculated value of the first regional impedance metric, a focal health condition of the patient, apply a subsequent regional electrical stimulus between an affecting electrode arranged at the conductive location and an affecting electrode, of a second regional pair of electrodes, arranged around the scalp of the patient, the second regional pair of electrodes corresponding to a second region of the patient, measure a subsequent electrical stimulus differential between an effected electrode arranged at the conductive location and an effected electrode of the second regional pair of electrodes, calculate, for the second region of the brain of the patient and based on the measured subsequent electrical stimulus differential, a value of a second regional impedance metric, compare the calculated value of the first regional impedance metric and the calculated value of the second regional impedance metric, and identify, based on the comparison, a differential focal health condition of the patient.

2. The system of claim 1, wherein the processing circuitry is further configured to identify the health condition of the patient by determining, based on the calculated value of the impedance metric, a differential impedance value relative to a reference impedance value selected from a library of reference impedance values, the reference value being selected based on biometrics of the patient, and identifying, based on the determined differential impedance value, the health condition of the patient.

3. The system of claim 1, wherein the processing circuitry is further configured to identify the focal health condition of the patient by comparing the calculated value of the first regional impedance metric to a reference value selected from a library of reference values, the reference value being selected based on biometrics of the patient, and identifying the focal health condition of the patient based on the comparison.

4. The system of claim 1, wherein the processing circuitry is further configured to identify the differential focal health condition of the patient by performing a ratiometric analysis as the comparison of the calculated value of the first regional impedance metric and the calculated value of the second regional impedance metric.

5. The system of claim 1, wherein the processing circuitry is further configured to calculate a time-averaged value of the impedance metric as the calculated value.

6. The system of claim 1, wherein the processing circuitry is further configured to calculate a rate of change of values of the impedance metric, over a predefined period of time, as the calculated value.

7. The system of claim 1, wherein the processing circuitry is further configured to apply an electrical current as the electrical stimulus between the two or more affecting electrodes, and measure a voltage potential as the electrical stimulus differential between the two or more effected electrodes.

8. The system of claim 7, wherein the processing circuitry is further configured to apply the electrical current at a value between 0.1 milliamperes and 10.0 milliamperes.

9. The system of claim 7, wherein the processing circuitry is further configured to apply the electrical current at multiple frequencies.

10. The system of claim 1, wherein the processing circuitry is further configured to apply the voltage potential at a value between 0.5 Volts and 3 Volts.

11. The system of claim 1, wherein the processing circuitry is further configured to identify the health condition of the patient as one of ischemic, hemorrhagic, or edemic.

12. A method for non-invasive intracranial monitoring, comprising:

applying, by processing circuitry, a voltage potential as an electrical stimulus between two or more affecting electrodes, the two or more affecting electrodes being arranged between a conductive location of a cranium of a patient and a location on a scalp of the patient;

measuring, by the processing circuitry, an electric current as an electrical stimulus differential between two or more effected electrodes, the two or more effected electrodes being arranged between the conductive location of the cranium of the patient and the location on the scalp of the patient;

calculating, by the processing circuitry and for the two or more effected electrodes, a value of an impedance metric;

identifying, by processing circuitry and based on the calculated value of the impedance metric, a health condition of the patient, applying a regional electrical stimulus between an affecting electrode arranged at the conductive location and one of the plurality of affecting electrodes arranged around the scalp of the patient and proximate one of the plurality of symmetrically-arranged effected electrodes, the two or more effected electrodes including a plurality of effected electrodes arranged symmetrically around the scalp of the patient, the two or more affecting electrodes including a plurality of affecting electrodes arranged around the scalp of the patient, one of the plurality of affecting electrodes being proximate one of the plurality of symmetrically-arranged effected electrodes, each one of the plurality of affecting electrodes and a respective one of the plurality of symmetrically-arranged effected electrodes defining a regional pair, the one of the plurality of affecting electrodes and the proximate one of the plurality of symmetrically-arranged effected electrodes defining a first regional pair of electrodes corresponding to a first region of a brain of the patient, measuring an electrical stimulus differential between an effected electrode arranged at the conductive location and the proximate one of the plurality of symmetrically-arranged effected electrodes of the first regional pair of electrodes, calculating, for the first region of the brain of the patient and based on the measured electrical stimulus differential, a value of a first regional impedance metric, and identify, based on the calculated value of the first regional impedance metric, a focal health condition of the patient;

applying a subsequent regional electrical stimulus between an affecting electrode arranged at the conductive location and an affecting electrode, of a second regional pair of electrodes, arranged around the scalp of the patient, the second regional pair of electrodes corresponding to a second region of the patient, measuring a subsequent electrical stimulus differential between an effected electrode arranged at the conductive location and an effected electrode of the second regional pair of electrodes, calculating, for the second region of the brain of the patient and based on the measured subsequent electrical stimulus differential, a value of a second regional impedance metric, compare the calculated value of the first regional impedance metric and the calculated value of the second regional impedance metric, and identifying based on the comparison, a differential focal health condition of the patient.

13. The method of claim 12, wherein the applying the electrical stimulus between the two or more affecting electrodes includes applying the electrical stimulus via, as the conductive location of the cranium of the patient, one or more locations selected from a group including a right orbit, a left orbit, a soft palate, and a base of a neck of the patient.

14. A system for non-invasive intracranial monitoring, comprising:

electrodes arranged between a conductive location of a cranium of a patient and a location on a scalp of the patient; and processing circuitry configured to apply a voltage potential as an electrical stimulus between the electrodes, measure an electric current as an electrical stimulus differential between the electrodes, calculate, for the electrodes, a value of an impedance metric, and identify, based on the calculated value of the impedance metric, a health condition of the patient, wherein the electrodes include a plurality of electrodes arranged symmetrically around the scalp of the patient, each of the plurality of symmetrically-arranged electrodes around the scalp of the patient define a region of a brain of the patient, and the processing circuitry is further configured to apply a regional electrical stimulus between an electrode arranged at the conductive location and a first one of the plurality of symmetrically-arranged electrodes, the regional electrical stimulus being applied to a corresponding first region of the brain, measure an electrical stimulus differential between the electrode arranged at the conductive location and the first one of the plurality of symmetrically-arranged electrodes of the first region of the brain, calculate, for the first region of the brain of the patient and based on the measured electrical stimulus differential, a value of a first regional impedance metric, and identify, based on the calculated value of the first regional impedance metric, a focal health condition of the patient, apply a subsequent regional electrical stimulus between an affecting electrode arranged at the conductive location and an affecting electrode, of a second regional pair of electrodes, arranged around the scalp of the patient, the second regional pair of electrodes corresponding to a second region of the patient, measure a subsequent electrical stimulus differential between an effected electrode arranged at the conductive location and an effected electrode of the second regional pair of electrodes, calculate, for the second region of the brain of the patient and based on the measured subsequent electrical stimulus differential, a value of a second regional impedance metric, compare the calculated value of the first regional impedance metric and the calculated value of the second regional impedance metric, and identify, based on the comparison, a differential focal health condition of the patient.

15. The system of claim 14, wherein the processing circuitry is further configured to identify the health condition of the patient by determining, based on the calculated value of the impedance metric, a differential impedance value relative to a reference impedance value selected from a library of reference impedance values, the reference value being selected based on biometrics of the patient, and identifying, based on the determined differential impedance value, the health condition of the patient.

16. The system of claim 15, wherein the processing circuitry is further configured to identify the focal health condition of the patient by comparing the calculated value of the first regional impedance metric to a reference value selected from a library of reference values, the reference value being selected based on biometrics of the patient, and identifying the focal health condition of the patient based on the comparison.

* * * * *